(12) United States Patent
Sowards et al.

(10) Patent No.: US 12,725,536 B2
(45) Date of Patent: Sep. 1, 2026

(54) ULTRASOUND TRAINING SYSTEM

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 960 days.

(21) Appl. No.: 17/890,148

(22) Filed: Aug. 17, 2022

(65) Prior Publication Data

US 2024/0062678 A1 Feb. 22, 2024

(51) Int. Cl.

| | |
|---|---|
| ***G09B 23/30*** | (2006.01) |
| ***G09B 23/28*** | (2006.01) |
| *A61B 17/34* | (2006.01) |

(52) U.S. Cl.

CPC .... *G09B 23/286* (2013.01); *A61B 2017/3413* (2013.01)

(58) Field of Classification Search

CPC ....... G09B 23/28; G09B 23/286; G09B 23/30

See application file for complete search history.

(56) References Cited

U.S. PATENT DOCUMENTS

| | | |
|---|---|---|
| 4,311,138 A | 1/1982 | Sugarman |
| 4,971,068 A | 11/1990 | Sahi |
| 5,148,809 A | 9/1992 | Biegeleisen-Knight et al. |
| 5,181,513 A | 1/1993 | Touboul et al. |
| 5,325,293 A | 6/1994 | Dorne |

(Continued)

FOREIGN PATENT DOCUMENTS

| | | |
|---|---|---|
| AU | 2006201646 A1 | 11/2006 |
| CN | 114129137 B | 9/2022 |

(Continued)

OTHER PUBLICATIONS

U.S. Appl. No. 17/380,767, filed Jul. 20, 2021 Non-Final Office Action dated Mar. 6, 2023.

(Continued)

*Primary Examiner* — Kurt Fernstrom

(74) *Attorney, Agent, or Firm* — Rutan & Tucker LLP

(57) ABSTRACT

Disclosed herein is an ultrasound training system that according to various embodiments includes an ultrasound probe, a vascular access device, and a patient simulation block. Logic of the system tracks the location and orientation of the probe and the vascular access device via magnetic tracking, fiber optic shape sensing, inertia measurement or any combination thereof. The logic depicts the vascular access device in relation to the patient simulation block on a display along with a simulated ultrasound image. The patient simulation block may include artificial anatomical elements and the logic may depict simulated anatomic elements aligned with the artificial anatomical elements. The probe includes a load sensor and the logic depicts an anatomic element having a shape affected by the load. The vascular access device includes magnetic elements defining a magnetic signature and the logic depicts the type and/or size of the vascular access device based on the magnetic signature.

19 Claims, 7 Drawing Sheets

(56) References Cited

U.S. PATENT DOCUMENTS 5,441,052 A 8/1995 Miyajima
5,549,554 A 8/1996 Miraki
5,573,529 A 11/1996 Haak et al.
5,775,322 A 7/1998 Silverstein et al.
5,879,297 A 3/1999 Haynor et al.
5,908,387 A 6/1999 LeFree et al.
5,967,984 A 10/1999 Chu et al.
5,970,119 A 10/1999 Hofmann
6,004,270 A 12/1999 Urbano et al.
6,019,724 A 2/2000 Gronningsaeter et al.
6,068,599 A 5/2000 Saito et al.
6,074,367 A 6/2000 Hubbell
6,129,668 A 10/2000 Haynor et al.
6,132,379 A 10/2000 Patacsil et al.
6,216,028 B1 4/2001 Haynor et al.
6,233,476 B1 5/2001 Strommer et al.
6,245,018 B1 6/2001 Lee
6,263,230 B1 7/2001 Haynor et al.
6,375,615 B1 4/2002 Flaherty et al.
6,436,043 B2 8/2002 Bonnefous
6,498,942 B1 12/2002 Esenaliev et al.
6,503,205 B2 1/2003 Manor et al.
6,508,769 B2 1/2003 Bonnefous
6,511,458 B2 1/2003 Milo et al.
6,524,249 B2 2/2003 Moehring et al.
6,543,642 B1 4/2003 Milliorn
6,554,771 B1 4/2003 Buil et al.
6,592,520 B1 7/2003 Peszynski et al.
6,592,565 B2 7/2003 Twardowski
6,601,705 B2 8/2003 Molina et al.
6,612,992 B1 9/2003 Hossack et al.
6,613,002 B1 9/2003 Clark et al.
6,623,431 B1 9/2003 Sakuma et al.
6,641,538 B2 11/2003 Nakaya et al.
6,647,135 B2 11/2003 Bonnefous
6,687,386 B1 2/2004 Ito et al.
6,749,569 B1 6/2004 Pellegretti
6,754,608 B2 6/2004 Svanerudh et al.
6,755,789 B2 6/2004 Stringer et al.
6,840,379 B2 1/2005 Franks-Farah et al.
6,857,196 B2 2/2005 Dalrymple
6,979,294 B1 12/2005 Selzer et al.
7,074,187 B2 7/2006 Selzer et al.
7,244,234 B2 7/2007 Ridley et al.
7,359,554 B2 4/2008 Klingensmith et al.
7,534,209 B2 5/2009 Abend et al.
7,599,730 B2 10/2009 Hunter et al.
7,637,870 B2 12/2009 Flaherty et al.
7,681,579 B2 3/2010 Schwartz
7,691,061 B2 4/2010 Hirota
7,699,779 B2 4/2010 Sasaki et al.
7,720,520 B2 5/2010 Willis
7,727,153 B2 6/2010 Fritz et al.
7,734,326 B2 6/2010 Pedain et al.
7,831,449 B2 11/2010 Ying et al.
7,905,837 B2 3/2011 Suzuki
7,925,327 B2 4/2011 Weese
7,927,278 B2 4/2011 Selzer et al.
8,014,848 B2 9/2011 Birkenbach et al.
8,050,523 B2 11/2011 Younge et al.
8,060,181 B2 11/2011 Rodriguez Ponce et al.
8,068,581 B2 11/2011 Boese et al.
8,075,488 B2 12/2011 Burton
8,090,427 B2 1/2012 Eck et al.
8,105,239 B2 1/2012 Specht
8,172,754 B2 5/2012 Watanabe et al.
8,175,368 B2 5/2012 Sathyanarayana
8,200,313 B1 6/2012 Rambod et al.
8,211,023 B2 7/2012 Swan et al.
8,228,347 B2 7/2012 Beasley et al.
8,298,147 B2 10/2012 Huennekens et al.
8,303,505 B2 11/2012 Webler et al.
8,323,202 B2 12/2012 Roschak et al.
8,328,727 B2 12/2012 Miele et al.
8,388,541 B2 3/2013 Messerly et al.
8,409,103 B2 4/2013 Grunwald et al.
8,449,465 B2 5/2013 Nair et al.
8,553,954 B2 10/2013 Saikia
8,556,815 B2 10/2013 Pelissier et al.
8,585,600 B2 11/2013 Liu et al.
8,622,913 B2 1/2014 Dentinger et al.
8,706,457 B2 4/2014 Hart et al.
8,727,988 B2 5/2014 Flaherty et al.
8,734,357 B2 5/2014 Taylor
8,744,211 B2 6/2014 Owen
8,754,865 B2 6/2014 Merritt et al.
8,764,663 B2 7/2014 Smok et al.
8,781,194 B2 7/2014 Malek et al.
8,781,555 B2 7/2014 Burnside et al.
8,790,263 B2 7/2014 Randall et al.
8,849,382 B2 9/2014 Cox et al.
8,939,908 B2 1/2015 Suzuki et al.
8,961,420 B2 2/2015 Zhang
9,022,940 B2 5/2015 Meier
9,138,290 B2 9/2015 Hadjicostis
9,155,517 B2 10/2015 Dunbar et al.
9,204,858 B2 12/2015 Pelissier et al.
9,220,477 B2 12/2015 Urabe et al.
9,257,220 B2 2/2016 Nicholls et al.
9,295,447 B2 3/2016 Shah
9,320,493 B2 4/2016 Visveshwara
9,357,980 B2 6/2016 Toji et al.
9,364,171 B2 6/2016 Harris et al.
9,427,207 B2 8/2016 Sheldon et al.
9,445,780 B2 9/2016 Hossack et al.
9,456,766 B2 10/2016 Cox et al.
9,456,804 B2 10/2016 Tamada
9,459,087 B2 10/2016 Dunbar et al.
9,468,413 B2 10/2016 Hall et al.
9,492,097 B2 11/2016 Wilkes et al.
9,521,961 B2 12/2016 Silverstein et al.
9,554,716 B2 1/2017 Burnside et al.
9,582,876 B2 2/2017 Specht
9,597,008 B2 3/2017 Henkel et al.
9,610,061 B2 4/2017 Ebbini et al.
9,636,031 B2 5/2017 Cox
9,649,037 B2 5/2017 Lowe et al.
9,649,048 B2 5/2017 Cox et al.
9,702,969 B2 7/2017 Hope Simpson et al.
9,715,757 B2 7/2017 Ng et al.
9,717,415 B2 8/2017 Cohen et al.
9,731,066 B2 8/2017 Liu et al.
9,814,433 B2 11/2017 Benishti et al.
9,814,531 B2 11/2017 Yagi et al.
9,861,337 B2 1/2018 Patwardhan et al.
9,895,138 B2 2/2018 Sasaki
9,913,605 B2 3/2018 Harris et al.
9,949,720 B2 4/2018 Southard et al.
10,010,379 B1 7/2018 Gibby et al.
10,043,272 B2 8/2018 Forzoni et al.
10,380,919 B2 8/2019 Savitsky et al.
10,380,920 B2 8/2019 Savitsky et al.
10,424,225 B2 9/2019 Nataneli et al.
10,434,278 B2 10/2019 Dunbar et al.
10,449,330 B2 10/2019 Newman et al.
10,524,691 B2 1/2020 Newman et al.
10,636,323 B2 4/2020 Buras et al.
10,674,935 B2 6/2020 Henkel et al.
10,751,509 B2 8/2020 Misener
10,758,155 B2 9/2020 Henkel et al.
10,765,343 B2 9/2020 Henkel et al.
10,796,605 B2 10/2020 Buras et al.
10,818,199 B2 10/2020 Buras et al.
10,835,207 B2 11/2020 Altmann et al.
10,869,727 B2 12/2020 Yanof et al.
10,896,628 B2 1/2021 Savitsky et al.
11,011,078 B2 5/2021 Buras et al.
11,017,694 B2 5/2021 Buras et al.
11,017,695 B2 5/2021 Buras et al.
11,062,624 B2 7/2021 Savitsky et al.
11,120,709 B2 9/2021 Savitsky et al.
11,311,269 B2 4/2022 Dunbar et al.
11,315,439 B2 4/2022 Savitsky et al.
11,495,142 B2 * 11/2022 Petrinec ............... G09B 23/286

(56) References Cited

U.S. PATENT DOCUMENTS 11,600,201 B1 * 3/2023 Savitsky .............. A61B 8/4455
11,676,513 B2 6/2023 Buras et al.
12,062,297 B2 8/2024 Buras et al.
12,144,675 B2 11/2024 Durfee
12,396,656 B2 8/2025 Durfee et al.
12,414,835 B2 9/2025 Gibby et al.
2002/0038088 A1 3/2002 Imran et al.
2002/0148277 A1 10/2002 Umeda
2003/0028112 A1 2/2003 Paladini et al.
2003/0047126 A1 3/2003 Tomaschko
2003/0060714 A1 3/2003 Henderson et al.
2003/0073900 A1 4/2003 Senarith et al.
2003/0093001 A1 5/2003 Martikainen
2003/0106825 A1 6/2003 Molina et al.
2003/0120154 A1 6/2003 Sauer et al.
2003/0226868 A1 12/2003 Monden
2004/0055925 A1 3/2004 Franks-Farah et al.
2005/0000975 A1 1/2005 Carco et al.
2005/0049504 A1 3/2005 Lo et al.
2005/0165299 A1 7/2005 Kressy et al.
2005/0251030 A1 11/2005 Azar et al.
2005/0267365 A1 12/2005 Sokulin et al.
2006/0013523 A1 1/2006 Childlers et al.
2006/0015039 A1 1/2006 Cassidy et al.
2006/0020204 A1 1/2006 Serra et al.
2006/0079781 A1 4/2006 Germond-Rouet et al.
2006/0184029 A1 8/2006 Haim et al.
2006/0210130 A1 9/2006 Germond-Rouet et al.
2007/0043341 A1 2/2007 Anderson et al.
2007/0049822 A1 3/2007 Bunce et al.
2007/0073155 A1 3/2007 Park et al.
2007/0199848 A1 8/2007 Ellswood et al.
2007/0239120 A1 10/2007 Brock et al.
2007/0249911 A1 10/2007 Simon
2008/0021322 A1 1/2008 Stone et al.
2008/0033293 A1 2/2008 Beasley et al.
2008/0033759 A1 2/2008 Finlay
2008/0051657 A1 2/2008 Rold
2008/0146915 A1 6/2008 McMorrow
2008/0177186 A1 7/2008 Slater et al.
2008/0221425 A1 9/2008 Olson et al.
2008/0255475 A1 10/2008 Kondrosky et al.
2008/0294037 A1 11/2008 Richter
2008/0300491 A1 12/2008 Bonde et al.
2009/0012399 A1 1/2009 Sunagawa et al.
2009/0143672 A1 6/2009 Harms et al.
2009/0143684 A1 6/2009 Cermak et al.
2009/0156926 A1 6/2009 Messerly et al.
2009/0306509 A1 12/2009 Pedersen et al.
2010/0004539 A1 1/2010 Chen et al.
2010/0020926 A1 1/2010 Boese et al.
2010/0106015 A1 4/2010 Norris
2010/0160786 A1 6/2010 Nordgren et al.
2010/0179428 A1 7/2010 Pedersen et al.
2010/0211026 A2 8/2010 Sheetz et al.
2010/0277305 A1 11/2010 Garner et al.
2010/0286515 A1 11/2010 Gravenstein et al.
2010/0312121 A1 12/2010 Guan
2011/0002518 A1 1/2011 Ziv-Ari et al.
2011/0071404 A1 3/2011 Schmitt et al.
2011/0166451 A1 7/2011 Blaivas et al.
2011/0288405 A1 11/2011 Razavi et al.
2011/0295108 A1 12/2011 Cox et al.
2011/0313293 A1 12/2011 Lindekugel et al.
2012/0136242 A1 5/2012 Qi et al.
2012/0179038 A1 7/2012 Meurer et al.
2012/0197132 A1 8/2012 O'Connor
2012/0209121 A1 8/2012 Boudier
2012/0220865 A1 8/2012 Brown et al.
2012/0238875 A1 9/2012 Savitsky et al.
2012/0277576 A1 11/2012 Lui
2013/0041250 A1 2/2013 Pelissier et al.
2013/0102889 A1 4/2013 Southard et al.
2013/0131499 A1 5/2013 Chan et al.
2013/0131502 A1 5/2013 Blaivas et al.
2013/0150724 A1 6/2013 Blaivas et al.
2013/0188832 A1 7/2013 Ma et al.
2013/0218024 A1 8/2013 Boctor et al.
2013/0296651 A1 11/2013 Ito et al.
2013/0324840 A1 12/2013 Zhongping et al.
2014/0005530 A1 1/2014 Liu et al.
2014/0031690 A1 1/2014 Toji et al.
2014/0036091 A1 2/2014 Zalev et al.
2014/0073976 A1 3/2014 Fonte et al.
2014/0100440 A1 4/2014 Cheline et al.
2014/0155737 A1 6/2014 Manzke et al.
2014/0180098 A1 6/2014 Flaherty et al.
2014/0187920 A1 7/2014 Millett et al.
2014/0188133 A1 7/2014 Misener
2014/0188440 A1 7/2014 Donhowe et al.
2014/0257104 A1 9/2014 Dunbar et al.
2014/0276059 A1 9/2014 Sheehan
2014/0276081 A1 9/2014 Tegels
2014/0276085 A1 9/2014 Miller
2014/0276690 A1 9/2014 Grace
2014/0343431 A1 11/2014 Vajinepalli et al.
2015/0005738 A1 1/2015 Blacker
2015/0011887 A1 1/2015 Ahn et al.
2015/0065916 A1 3/2015 Maguire et al.
2015/0073279 A1 3/2015 Cai et al.
2015/0112200 A1 4/2015 Oberg et al.
2015/0157295 A1 6/2015 Liu et al.
2015/0209113 A1 7/2015 Burkholz et al.
2015/0209526 A1 7/2015 Matsubara et al.
2015/0294497 A1 10/2015 Ng et al.
2015/0297097 A1 10/2015 Matsubara et al.
2015/0305718 A1 10/2015 Ogasawara
2015/0327841 A1 11/2015 Banjanin et al.
2015/0359991 A1 12/2015 Dunbar et al.
2016/0029995 A1 2/2016 Navratil et al.
2016/0029998 A1 2/2016 Brister et al.
2016/0058420 A1 3/2016 Cinthio et al.
2016/0074015 A1 3/2016 Eda
2016/0100970 A1 4/2016 Brister et al.
2016/0101263 A1 4/2016 Blumenkranz et al.
2016/0113699 A1 4/2016 Sverdlik et al.
2016/0120607 A1 5/2016 Sorotzkin et al.
2016/0143622 A1 5/2016 Xie et al.
2016/0157808 A1 6/2016 Merritt et al.
2016/0166232 A1 6/2016 Merritt
2016/0202053 A1 7/2016 Walker et al.
2016/0213398 A1 7/2016 Liu
2016/0278743 A1 9/2016 Kawashima
2016/0278869 A1 9/2016 Grunwald
2016/0296208 A1 10/2016 Sethuraman et al.
2016/0374644 A1 12/2016 Mauldin, Jr. et al.
2017/0056062 A1 3/2017 Buljubasic
2017/0079548 A1 3/2017 Silverstein et al.
2017/0086785 A1 3/2017 Bjaerum
2017/0100092 A1 4/2017 Kruse et al.
2017/0164923 A1 6/2017 Matsumoto
2017/0172424 A1 6/2017 Eggers et al.
2017/0188839 A1 7/2017 Tashiro
2017/0196535 A1 7/2017 Arai et al.
2017/0215842 A1 8/2017 Ryu et al.
2017/0252002 A1 9/2017 Mine et al.
2017/0259013 A1 9/2017 Boyden et al.
2017/0265840 A1 9/2017 Bharat et al.
2017/0303894 A1 10/2017 Scully
2017/0367678 A1 12/2017 Sirtori et al.
2018/0015256 A1 1/2018 Southard et al.
2018/0116723 A1 5/2018 Hettrick et al.
2018/0125450 A1 5/2018 Blackbourne et al.
2018/0161502 A1 6/2018 Nanan et al.
2018/0199914 A1 7/2018 Ramachandran et al.
2018/0214119 A1 8/2018 Mehrmohammadi et al.
2018/0220993 A1 8/2018 Poland
2018/0225993 A1 8/2018 Buras et al.
2018/0228465 A1 8/2018 Southard et al.
2018/0235576 A1 8/2018 Brannan
2018/0250078 A1 9/2018 Shochat et al.
2018/0272108 A1 9/2018 Padilla et al.
2018/0279996 A1 10/2018 Cox et al.
2018/0286287 A1 * 10/2018 Razzaque .............. G01R 33/02

(56) References Cited

U.S. PATENT DOCUMENTS

| | | | | |
|---|---|---|---|---|
| 2018/0310955 | A1 | 11/2018 | Lindekugel et al. | |
| 2018/0317881 | A1 | 11/2018 | Astigarraga et al. | |
| 2018/0366035 | A1* | 12/2018 | Dunbar | A61B 6/037 |
| 2019/0060014 | A1 | 2/2019 | Hazelton et al. | |
| 2019/0069923 | A1 | 3/2019 | Wang | |
| 2019/0076121 | A1 | 3/2019 | Southard et al. | |
| 2019/0088019 | A1 | 3/2019 | Prevrhal et al. | |
| 2019/0105017 | A1 | 4/2019 | Hastings | |
| 2019/0117190 | A1 | 4/2019 | Djajadiningrat et al. | |
| 2019/0167148 | A1 | 6/2019 | Durfee et al. | |
| 2019/0223757 | A1 | 7/2019 | Durfee | |
| 2019/0223958 | A1 | 7/2019 | Kohli et al. | |
| 2019/0239850 | A1 | 8/2019 | Dalvin et al. | |
| 2019/0282262 | A1 | 9/2019 | Bouazza-Marouf et al. | |
| 2019/0282324 | A1 | 9/2019 | Freeman et al. | |
| 2019/0298457 | A1 | 10/2019 | Bharat | |
| 2019/0307419 | A1 | 10/2019 | Durfee | |
| 2019/0307516 | A1 | 10/2019 | Schotzko et al. | |
| 2019/0339525 | A1 | 11/2019 | Yanof et al. | |
| 2019/0355278 | A1 | 11/2019 | Sainsbury et al. | |
| 2019/0365348 | A1 | 12/2019 | Toume et al. | |
| 2020/0041261 | A1 | 2/2020 | Bernstein et al. | |
| 2020/0069285 | A1 | 3/2020 | Annangi et al. | |
| 2020/0069929 | A1 | 3/2020 | Mason et al. | |
| 2020/0113540 | A1 | 4/2020 | Gijsbers et al. | |
| 2020/0129136 | A1 | 4/2020 | Harding et al. | |
| 2020/0188028 | A1 | 6/2020 | Feiner et al. | |
| 2020/0230391 | A1 | 7/2020 | Burkholz et al. | |
| 2020/0305927 | A1 | 10/2020 | Grim et al. | |
| 2020/0367860 | A1 | 11/2020 | Rouet et al. | |
| 2021/0007710 | A1 | 1/2021 | Douglas | |
| 2021/0045716 | A1 | 2/2021 | Shiran et al. | |
| 2021/0161612 | A1 | 6/2021 | Black et al. | |
| 2021/0166583 | A1 | 6/2021 | Buras et al. | |
| 2021/0307838 | A1 | 10/2021 | Xia et al. | |
| 2021/0327303 | A1* | 10/2021 | Buras | A61B 8/467 |
| 2021/0353255 | A1 | 11/2021 | Schneider et al. | |
| 2021/0402144 | A1 | 12/2021 | Messerly | |
| 2022/0022969 | A1 | 1/2022 | Misener | |
| 2022/0031965 | A1 | 2/2022 | Durfee | |
| 2022/0039685 | A1 | 2/2022 | Misener et al. | |
| 2022/0039777 | A1 | 2/2022 | Durfee | |
| 2022/0054108 | A1 | 2/2022 | In 'T Groen et al. | |
| 2022/0096797 | A1 | 3/2022 | Prince | |
| 2022/0104886 | A1 | 4/2022 | Blanchard et al. | |
| 2022/0117582 | A1 | 4/2022 | McLaughlin et al. | |
| 2022/0160434 | A1 | 5/2022 | Messerly et al. | |
| 2022/0168050 | A1 | 6/2022 | Sowards et al. | |
| 2022/0172354 | A1 | 6/2022 | Misener et al. | |
| 2022/0211442 | A1* | 7/2022 | McLaughlin | A61B 17/3403 |
| 2022/0354462 | A1 | 11/2022 | Southworth et al. | |
| 2022/0381630 | A1 | 12/2022 | Sowards et al. | |
| 2022/0401157 | A1 | 12/2022 | Sowards et al. | |
| 2023/0053189 | A1 | 2/2023 | Geric et al. | |
| 2023/0113291 | A1 | 4/2023 | de Wild et al. | |
| 2023/0240643 | A1 | 8/2023 | Cermak et al. | |
| 2023/0389893 | A1 | 12/2023 | Misener et al. | |
| 2024/0008929 | A1 | 1/2024 | Misener et al. | |
| 2024/0050060 | A1 | 2/2024 | Kadokura et al. | |
| 2024/0050061 | A1 | 2/2024 | McLaughlin et al. | |
| 2024/0058074 | A1 | 2/2024 | Misener | |
| 2025/0000488 | A1 | 1/2025 | Misener et al. | |
| 2025/0032152 | A1 | 1/2025 | Miller et al. | |
| 2025/0057604 | A1 | 2/2025 | Blanchard et al. | |
| 2025/0064425 | A1 | 2/2025 | Durfee | |
| 2025/0143804 | A1 | 5/2025 | Misener | |
| 2025/0176942 | A1 | 6/2025 | McLaughlin et al. | |
| 2025/0339174 | A1 | 11/2025 | Durfee et al. | |

FOREIGN PATENT DOCUMENTS

| | | | |
|---|---|---|---|
| EP | 0933063 | A1 | 8/1999 |
| EP | 1504713 | A1 | 2/2005 |
| EP | 1591074 | B1 | 5/2008 |
| EP | 3181083 | A1 | 6/2017 |
| EP | 3530221 | A1 | 8/2019 |
| JP | 2000271136 | A | 10/2000 |
| JP | 2014150928 | A | 8/2014 |
| JP | 2018175547 | A | 11/2018 |
| KR | 20180070878 | A | 6/2018 |
| KR | 20190013133 | A | 2/2019 |
| KR | 20220141308 | A | 10/2022 |
| WO | 2013059714 | A1 | 4/2013 |
| WO | 2014/115150 | A1 | 7/2014 |
| WO | 2014174305 | A2 | 10/2014 |
| WO | 2015/017270 | A1 | 2/2015 |
| WO | 2017096487 | A1 | 6/2017 |
| WO | 2017214428 | A1 | 12/2017 |
| WO | 2018/026878 | A1 | 2/2018 |
| WO | 2018134726 | A1 | 7/2018 |
| WO | 2018206473 | A1 | 11/2018 |
| WO | 2019/232451 | A1 | 12/2019 |
| WO | 2020/002620 | A1 | 1/2020 |
| WO | 2020/016018 | A1 | 1/2020 |
| WO | 2019/232454 | A9 | 2/2020 |
| WO | 2020/044769 | A1 | 3/2020 |
| WO | 2020102665 | A1 | 5/2020 |
| WO | 2020/186198 | A1 | 9/2020 |
| WO | 2022/031762 | A1 | 2/2022 |
| WO | 2022/072727 | A2 | 4/2022 |
| WO | 2022/081904 | A1 | 4/2022 |
| WO | 2022-203713 | A2 | 9/2022 |
| WO | 2022263763 | A1 | 12/2022 |
| WO | 2023235435 | A1 | 12/2023 |
| WO | 2024010940 | A1 | 1/2024 |
| WO | 2024039608 | A1 | 2/2024 |
| WO | 2024039719 | A1 | 2/2024 |
| WO | 2025024821 | A1 | 1/2025 |
| WO | 2025231303 | A1 | 11/2025 |

OTHER PUBLICATIONS

U.S. Appl. No. 17/393,283, filed Aug. 3, 2021 Non-Final Office Action dated Mar. 31, 2023.

U.S. Appl. No. 17/491,308, filed Sep. 30, 2021 Restriction Requirement dated Feb. 27, 2023.

Ezono, eZSimulator, https://www.ezono.com/en/ezsimulator/, last accessed Sep. 13, 2022.

Ikhsan Mohammad et al: "Assistive technology for ultrasound-guided central venous catheter placement", Journal of Medical Ultrasonics, Japan Society of Ultrasonics in Medicine, Tokyo, JP, vol. 45, No. 1, Apr. 19, 2017, pp. 41-57, XPO36387340, ISSN: 1346-4523, DOI: 10.1007/S10396-017-0789-2 [retrieved on Apr. 19, 2017].

Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).

Pagoulatos, N. et al. "New spatial localizer based on fiber optics with applications in 3D ultrasound imaging" Proceeding of Spie, vol. 3976 (Apr. 18, 2000; Apr. 18, 2000).

PCT/US2021/042369 filed Jul. 20, 2021 International Search Report and Written Opinion dated Oct. 25, 2021.

PCT/US2021/044419 filed Aug. 3, 2021 International Search Report and Written Opinion dated Nov. 19, 2021.

PCT/US2021/045218 filed Aug. 9, 2021 International Search Report and Written Opinion dated Nov. 23, 2021.

PCT/US2021/053018 filed Sep. 30, 2021 International Search Report and Written Opinion dated May 3, 2022.

PCT/US2021/055076 filed Oct. 14, 2021 International Search Report and Written Opinion dated Mar. 25, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docld/1235/file/SebastianVogtDissertation.pdf.

Sonosim, https://sonosim.com/ultrasound-simulation/? last accessed Sep. 13, 2022.

U.S. Appl. No. 17/397,486, filed Aug. 9, 2021 Restriction Requirement dated Aug. 12, 2022.

(56) References Cited

OTHER PUBLICATIONS

William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
PCT/US2021/050973 filed Sep. 17, 2021 International Search Report and Written Opinion dated Nov. 7, 2022.
U.S. Appl. No. 17/380,767, filed Jul. 20, 2021 Restriction Requirement dated Dec. 15, 2022.
U.S. Appl. No. 17/393,283, filed Aug. 3, 2021 Restriction Requirement dated Jan. 12, 2023.
U.S. Appl. No. 17/397,486, filed Aug. 9, 2021 Non-Final Office Action dated Jan. 23, 2023.
U.S. Appl. No. 17/501,909, filed Oct. 14, 2021 Restriction Requirement dated Feb. 1, 2023.
Stolka, P.J., et al., (2014). Needle Guidance Using Handheld Stereo Vision and Projection for Ultrasound-Based Interventions. In: Galland, P., Hata, N., Barillot, C., Hornegger, J., Howe, R. (eds) Medical Image Computing and Computer-Assisted Intervention—MICCAI 2014. MICCAI 2014. (Year: 2014).
U.S. Appl. No. 17/491,308, filed Sep. 30, 2021 Non-Final Office Action dated Jun. 5, 2023.
U.S. Appl. No. 17/501,909, filed Oct. 14, 2021 Non-Final Office Action dated Jun. 6, 2023.
U.S. Appl. No. 17/832,389, filed Jun. 3, 2022 Restriction Requirement dated Jul. 13, 2023.
U.S. Appl. No. 17/393,283, filed Aug. 3, 2021 Non-Final Office Action dated Feb. 29, 2024.
U.S. Appl. No. 17/397,486, filed Aug. 9, 2021 Non-Final Office Action dated Mar. 1, 2024.
U.S. Appl. No. 17/491,308, filed Sep. 30, 2021 Non-Final Office Action dated Mar. 22, 2024.
U.S. Appl. No. 17/501,909, filed Oct. 14, 2021 Advisory Action dated Jan. 24, 2024.
U.S. Appl. No. 17/501,909, filed Oct. 14, 2021 Non-Final Office Action dated Mar. 21, 2024.
U.S. Appl. No. 17/832,389, filed Jun. 3, 2022 Advisory Action dated Apr. 4, 2024.
U.S. Appl. No. 17/832,389, filed Jun. 3, 2022 Final Office Action dated Jan. 25, 2024.
U.S. Appl. No. 17/861,031, filed Jul. 8, 2022 Final Office Action dated Mar. 15, 2024.
PCT/US2023/030160 filed Aug. 14, 2023 International Search Report and Written Opinion dated Oct. 23, 2023.
PCT/US2023/030347 filed Aug. 16, 2023 International Search Report and Written Opinion dated Nov. 6, 2023.
Practical guide for safe central venous catheterization and management 2017 Journal of Anesthesia vol. 34 published online Nov. 30, 2019 pp. 167-186.
U.S. Appl. No. 17/393,283, filed Aug. 3, 2021 Advisory Action dated Jan. 19, 2024.
U.S. Appl. No. 17/478,754, filed Sep. 17, 2021 Restriction Requirement dated Jan. 22, 2024.
U.S. Appl. No. 17/501,909, filed Oct. 14, 2021 Final Office Action dated Nov. 21, 2023.
PCT/US2024/039922 filed Jul. 26, 2024 International Search Report and Written Opinion dated Jan. 9, 2025.
U.S. Appl. No. 17/478,754, filed Sep. 17, 2021 Non-Final Office Action dated Dec. 30, 2024.
U.S. Appl. No. 17/888,359, filed Aug. 15, 2022 Non-Final Office Action dated Feb. 12, 2025.
PCT/US2023/024067 filed May 31, 2023 International Search Report and Written Opinion dated Sep. 15, 2023.
PCT/US2023/027147 filed Jul. 7, 2023 International Search Report and Written Opinion dated Oct. 2, 2023.
State, A., et al. (Aug. 1996). Technologies for augmented reality systems: Realizing ultrasound-guided needle biopsies. In Proceedings of the 23rd annual conference on computer graphics and interactive techniques (pp. 439-446) (Year: 1996).
U.S. Appl. No. 17/380,767, filed Jul. 20, 2021 Notice of Allowance dated Aug. 31, 2023.
U.S. Appl. No. 17/393,283, filed Aug. 3, 2021 Final Office Action dated Oct. 16, 2023.
U.S. Appl. No. 17/397,486, filed Aug. 9, 2021 Advisory Action dated Oct. 5, 2023.
U.S. Appl. No. 17/397,486, filed Aug. 9, 2021 Final Office Action dated Aug. 4, 2023.
U.S. Appl. No. 17/491,308, filed Sep. 30, 2021 Board Decison dated Oct. 25, 2023.
U.S. Appl. No. 17/491,308, filed Sep. 30, 2021 Final Office Action dated Aug. 29, 2023.
U.S. Appl. No. 17/832,389, filed Jun. 3, 2022 Non-Final Office Action dated Oct. 6, 2023.
U.S. Appl. No. 17/861,031, filed Jul. 8, 2022 Non-Final Office Action dated Sep. 14, 2023.
U.S. Appl. No. 17/393,283, filed Aug. 3, 2021 Notice of Allowance dated Sep. 18, 2024.
U.S. Appl. No. 17/397,486, filed Aug. 9, 2021 Notice of Allowance dated Jul. 10, 2024.
U.S. Appl. No. 17/478,754, filed Sep. 17, 2021 Non-Final Office Action dated Jul. 1, 2024.
U.S. Appl. No. 17/491,308, filed Sep. 30, 2021 Notice of Allowance dated Jun. 27, 2024.
U.S. Appl. No. 17/501,909, filed Oct. 14, 2021 Final Office Action dated Aug. 5, 2024.
U.S. Appl. No. 17/501,909, filed Oct. 14, 2021 Notice of Allowance dated Sep. 25, 2024.
U.S. Appl. No. 17/832,389, filed Jun. 3, 2022 Notice of Allowance dated May 15, 2024.
U.S. Appl. No. 17/861,031, filed Jul. 8, 2022 Advisory Action dated Jun. 7, 2024.
U.S. Appl. No. 17/861,031, filed Jul. 8, 2022 Notice of Allowance dated Jul. 3, 2024.
U.S. Appl. No. 17/888,359, filed Aug. 15, 2022 Restriction Requirement dated Sep. 5, 2024.
U.S. Appl. No. 18/385,101, filed Oct. 30, 2023 Notice of Allowance dated Aug. 20, 2024.
Manuel Birlo et al: "Utility of Optical See-Through Head Mounted Displays in Augmented Reality-Assisted Surgery: A systematic review", arxiv.org, Cornell University Library, 201 Olin Library Cornell University Ithaca, NY 14853, Feb. 8, 2022 (Feb. 8, 2022), XP091157128, DOI: 10.1016/J.MEDIA.2022.102361 Section 8.5, section 8.2.
PCT/US2025/027390 filed May 1, 2025 International Search Report and Written Opinion dated Jul. 29, 2025.
U.S. Appl. No. 17/478,754, filed Sep. 17, 2021 Advisory Action dated Jun. 24, 2025.
U.S. Appl. No. 17/478,754, filed Sep. 17, 2021 Final Office Action dated Apr. 11, 2025.
U.S. Appl. No. 17/478,754, filed Sep. 17, 2021 Notice of Allowance dated Aug. 14, 2025.
U.S. Appl. No. 17/888,359, filed Aug. 15, 2022 Advisory Action dated Sep. 3, 2025.
U.S. Appl. No. 17/888,359, filed Aug. 15, 2022 Final Office Action dated Jun. 18, 2025.
U.S. Appl. No. 17/888,359, filed Aug. 15, 2022 Notice of Allowance dated Oct. 21, 2025.
U.S. Appl. No. 18/652,728, filed May 1, 2024 Non-Final Office Action dated Oct. 1, 2025.
U.S. Appl. No. 18/885,090, filed Sep. 13, 2024 Non-Final Office Action dated Sep. 29, 2025.
U.S. Appl. No. 18/936,364, filed Nov. 4, 2024 Non-Final Office Action dated Feb. 5, 2025.
U.S. Appl. No. 18/652,728, filed May 1, 2024 Final Office Action dated Apr. 3, 2026.
U.S. Appl. No. 18/786,361, filed Jul. 26, 2024 Non-Final Office Action dated Jan. 28, 2026.
U.S. Appl. No. 18/885,090, filed Sep. 13, 2024 Notice of Allowance dated Mar. 10, 2026.
U.S. Appl. No. 18/936,364, filed Nov. 4, 2024 Notice of Allowance dated Mar. 3, 2026.

(56) References Cited

OTHER PUBLICATIONS

U.S. Appl. No. 19/019,042, filed Jan. 13, 2025 Notice of Allowance dated Feb. 4, 2026.
U.S. Appl. No. 19/043,025, filed Jan. 31, 2025 Non-Final Office Action dated Apr. 7, 2026.

* cited by examiner

ULTRASOUND TRAINING SYSTEM

BACKGROUND

Ultrasound imaging has provided a significant advantage in the performance of various procedures. Some procedures that utilize ultrasound imaging may be invasive to a patient therefore pose a risk to the patient is not performed properly. As such, the clinicians may rely on the ultrasound imaging for guidance in the performance of the procedures. In some instances, obtaining an ultrasound image and performing the procedure may be done by the same clinician. For example, the clinician may hold the ultrasound probe with one hand while inserting a needle into a blood vessel with the other hand. In some instances, it may require significant training for a clinician to become proficient with such procedures. However, the invasive nature and risk associated with some procedures, such as a vascular access, pose a significant risk to the patient if training is attempted during actual procedures. As such, there is a need for a training system so that clinicians may be trained without posing a risk to the patients.

Disclosed herein is a system for training clinicians in performing vascular access procedures utilizing ultrasound imaging.

SUMMARY

Briefly summarized, disclosed herein is an ultrasound training system, according to some embodiments. The system includes (i) an ultrasound probe, (ii) a patient simulation block configured for engagement with the ultrasound probe, and (iii) a system module coupled with the ultrasound probe. The system module includes a console having a number of processors and a non-transitory computer readable medium having logic stored thereon that when executed by the processors performs operations of the system. The operations include obtaining a position and an orientation of the ultrasound probe with respect to the patient simulation block and depicting a simulated ultrasound image of one or more anatomical elements on a display of the system based on the position and orientation of the ultrasound probe. In some embodiments, the operations further include dynamically adjusting the simulated ultrasound image based on at least one of dynamic repositioning or reorienting of the ultrasound probe.

In some embodiments, the anatomical elements include a blood vessel.

In some embodiments, the ultrasound probe includes a load sensor, where the load sensor is configured to determine a contact force magnitude between the ultrasound probe and the patient simulation block, and the operations further include adjusting a shape of the one or more anatomical elements depicted in the simulated ultrasound image based on the contact force magnitude.

In some embodiments, the system further incudes a vascular access device (VAD) operatively coupled with the system module, where the VAD is configured for positioning and orienting by a trainee with respect to the patient simulation block, and where the operations further include (i) obtaining a position and an orientation of the VAD with respect to the patient simulation block and (ii) overlaying a simulated image of the VAD atop the simulated ultrasound image. In some embodiments, the operations further include dynamically adjusting the simulated ultrasound image of the VAD based on at least one of dynamic repositioning or reorienting of the VAD.

In some embodiments, the system further includes a plurality of magnetic field sensors operatively coupled with the system module, and obtaining the position and the orientation of the ultrasound probe includes determining a position and an orientation of one or more magnetic elements of the ultrasound probe via the magnetic field sensors.

In some embodiments, obtaining the position and the orientation of the VAD includes determining a position and an orientation of one or more magnetic elements of the VAD via the magnetic field sensors.

In some embodiments, the magnetic field sensors are physically coupled with the patient simulation block.

In some embodiments, the ultrasound probe includes an inertial measurement unit (IMU) operatively coupled with the system module, and obtaining the position and the orientation of the ultrasound probe further includes determining at least one of the position or the orientation of the ultrasound probe based on data received from the IMU.

In some embodiments, the system further includes a first optical fiber coupled between the system module and the ultrasound probe. The first optical fiber includes one or more core fibers including a plurality of sensors distributed along a longitudinal length of a corresponding core fiber and each sensor of the plurality of sensors being configured to (i) reflect a light signal of a different spectral width based on received incident light, and (ii) change a characteristic of the reflected light signal based on a shape of the first optical fiber, and the operations further include (i) providing an incident light signal to the first optical fiber, (ii) receiving reflected light signals of different spectral widths of the incident light from one or more of the plurality of sensors, and (iii) processing the reflected light signals associated with the one or more of core fibers to determine a three-dimensional (3D) shape of the first optical fiber.

In some embodiments, the first optical fiber is (i) physically coupled with ultrasound probe at a distal end of the optical fiber and (ii) physically coupled with the patient simulation block at the distal end of the optical fiber, and obtaining the position and the orientation of the ultrasound probe with respect to the patient simulation block includes determining the position and the orientation of the ultrasound probe based on the shape of the first optical fiber.

In some embodiments, the system further includes a second optical fiber coupled between the system module and the VAD. The second optical fiber includes one or more core fibers including a plurality of sensors distributed along a longitudinal length of a corresponding core fiber and each sensor of the plurality of sensors being configured to (i) reflect a light signal of a different spectral width based on received incident light, and (ii) change a characteristic of the reflected light signal based on a shape of the second optical fiber, and the operations further include (i) providing an incident light signal to the second optical fiber, (ii) receiving reflected light signals of different spectral widths of the incident light from one or more of the plurality of sensors, and (iii) processing the reflected light signals associated with the one or more of core fibers to determine a three-dimensional (3D) shape of the second optical fiber.

In some embodiments, the second optical fiber is (i) physically coupled with the VAD at a distal end of the second optical fiber and (ii) physically coupled with the patient simulation block at the distal end of the second optical fiber, and obtaining the position and the orientation of the VAD with respect to the patient simulation block includes determining the position and the orientation of the VAD based on the shape of the second optical fiber.

In some embodiments, the patient simulation block includes one or more artificial anatomic elements disposed therein, and operations further include aligning the one or more anatomical elements of the computer generated image with the one or more artificial anatomical elements.

In some embodiments, the patient simulation block is configured to receive the VAD inserted therein including insertion within at least one of the one or more artificial anatomic elements, and overlaying the simulated image of the VAD atop the simulated ultrasound image includes depicting the VAD inserted within at least one of the one or more anatomic elements aligned with the at least one of the one or more artificial anatomic elements.

In some embodiments, the ultrasound probe is configured to obtain an actual ultrasound image of the patient simulation block including the one or more artificial anatomic elements, and the simulated ultrasound image includes the actual ultrasound image of the patient simulation block.

In some embodiments, the one or more magnetic elements of the VAD define a magnetic signature of the VAD, and the operations further include defining at least one of a type or a size of the VAD depicted in simulated image of the VAD based on the magnetic signature.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which.

DETAILED DESCRIPTION

Figure 1A:
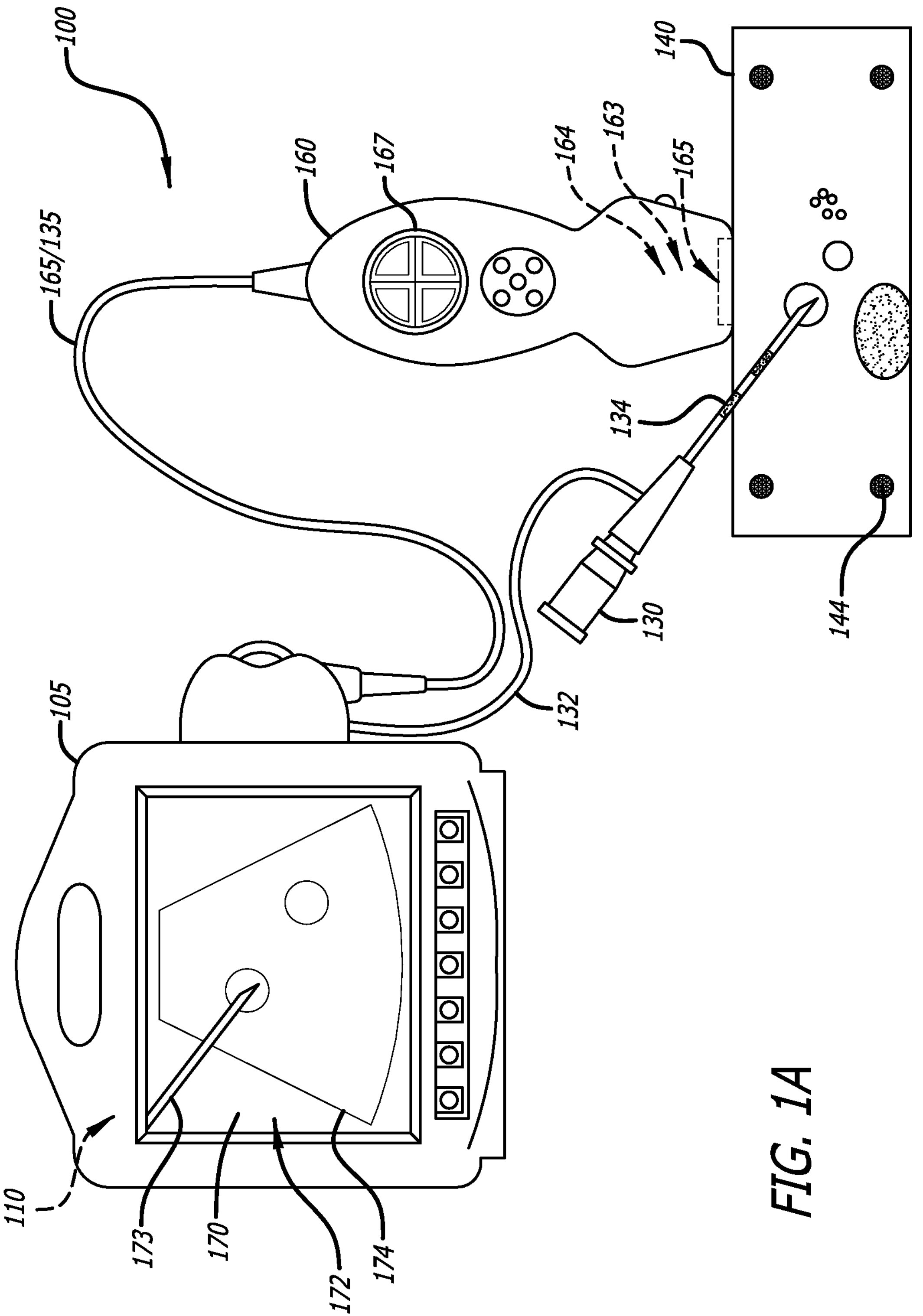
FIG. 1A is an illustrative embodiment of an ultrasound training system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The phrases "connected to," "coupled with," and "in communication with" refer to any form of interaction between two or more entities, including but not limited to mechanical, electrical, magnetic, electromagnetic, wireless, and optical interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is the portion at the opposite end. For example, the proximal end of an elongate probe guide is defined as the end closest to the clinician during utilization of the elongate probe. The distal end is the end opposite the proximal end, along the longitudinal direction of the elongate probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random-access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

FIG. 1A illustrates an embodiment of an ultrasound training system, according to some embodiments. The ultrasound training system (system) 100 is generally configured for defining a simulated use environment for an ultrasound probe while performing medical treatments on a patient such as, for example, the access of a patient vasculature as illustrated. The system 100 generally includes a system module 105 having a console 110 operatively coupled with an ultrasound probe (probe) 160 via a probe cable 162.

The probe 160 may be an actual ultrasound probe or model of an ultrasound probe having a number of ultrasound probe features as further described below. The probe 160 is configured for tracking by the system module 105. In other words, the system module 105 is configured to determine a position and an orientation of the probe 160 in 3D space as further described below. The probe 160 may include components that allow for tracking of the probe 160 by the system module 105 via the utilization of corresponding components of the system module 105 and/or the probe 160. For example, the probe 160 may include a number (e.g., 1, 2, 3 or more) magnets or magnetized components 164 that are detectable and/or trackable via a number (e.g., 1, 2, 3 or more) magnetic field sensors 144 operatively coupled with the system module 105.

In some embodiments, the probe 160 may further include the control buttons 167 for controlling certain aspects of the system 100 during an ultrasound training procedure, thus eliminating the need for the clinician to physically interact with the system module 105. For example, a control button of the control buttons 167 can be configured to select or lock onto a simulated target (e.g., a blood vessel) when pressed for visualization of the target in preparation for simulating inserting a VAD 130. The control buttons 167 can also be configured to define operation of the system 100 in other ways.

The system 100 may further include a vascular access device (VAD) 130 or model of a VAD. The VAD 130 may take the form any device for accessing the vasculature of a patient, such as the needle (illustrated), a stylet, a guidewire, or a catheter, for example. The VAD 130 may include components that allow for tracking of the VAD 130 by the system module 105 via the utilization of corresponding components of the system module 105 and/or the probe 160. For example, the VAD 130 may include a number (e.g., 1, 2, 3 or more) magnets or magnetized components 134 that are detectable and/or trackable via a number (e.g., 1, 2, 3 or more) magnetic field sensors 144 operatively coupled with the system module 105. In some embodiments, the magnetic field sensors 144 may be physically attached to the system module 105 or the probe 160. In some embodiments, the magnetized components 134 may define a magnetic signature of the VAD 130, where the magnetic signature defines a type or size of the VAD 130. In some embodiments, the VAD 130 may be coupled with the system module 105 or the probe 160 via a VAD cable 132.

In other words, the system module 105 is configured to determine a position and an orientation of the probe 160 in 3D space or in relation to the VAD 130 and/or the patient simulation block 140. In some embodiments, the VAD 130 may include a number of magnetized components 134 (e.g., magnets) to facilitate tracking of the VAD 130.

The system 100 may further include a patient simulation block 140. The patient simulation block 140 may be configured to represent a portion of the patient. The patient simulation block 140 may be formed of a material that simulates body tissue and may be configured for puncture by the VAD 130. In some embodiments, the patient simulation block 140 may include artificial anatomic elements, such as a bones, blood vessels, nerve bundles, for example. In some embodiments, the artificial anatomic elements may include physical attributes, e.g., a bone may be formed of a hard material within the patient simulation block 140. Similarly, a blood vessel may include a void within the block material. The patient simulation block 140 may include other function components, such as magnets, or sensors, for example, as further described below. In some embodiments, the patient simulation block 140 may include a number (e.g., 1, 2, 3 or more) of magnetic field sensors 144 operatively coupled with the system module 105, such as via a wired or wireless connection.

In various embodiments, the probe 160 may include components to facilitate tracking of the probe 160. In some embodiments, the probe 160 may include a number of magnetic tracking components 164, e.g., a number of magnets or a number of magnetic field sensors. In some embodiments, the probe 160 may include an inertial measurement unit ("IMU") 163 that includes one or more components, such as an accelerometer, or a gyroscope, for example to further track the probe 160.

The probe 160 may also include a load sensor 165 configured to determine a compression load magnitude applied to the patient simulation block 140 during use. Acquiring ultrasound images typically requires intimate contact of the head of an ultrasound probe with the patient. In some instances, the clinician may cause a depression the ultrasound probe into the patient so as to position of the ultrasound probe to obtain a desired ultrasound image. In some instance, the depression of the probe may alter the shape of anatomic elements beneath the patient's skin, such as a vein, for example.

During use, a clinician in training performs a simulated vascular access procedure (or other procedure) utilizing the components of the system 100 while a simulated image 172 is depicted on the display 170 of the system module 105. In one embodiments, the simulated image 172 may include a simulated VAD image 173 overlayed atop a simulated ultrasound image 174.

Figure 1B:
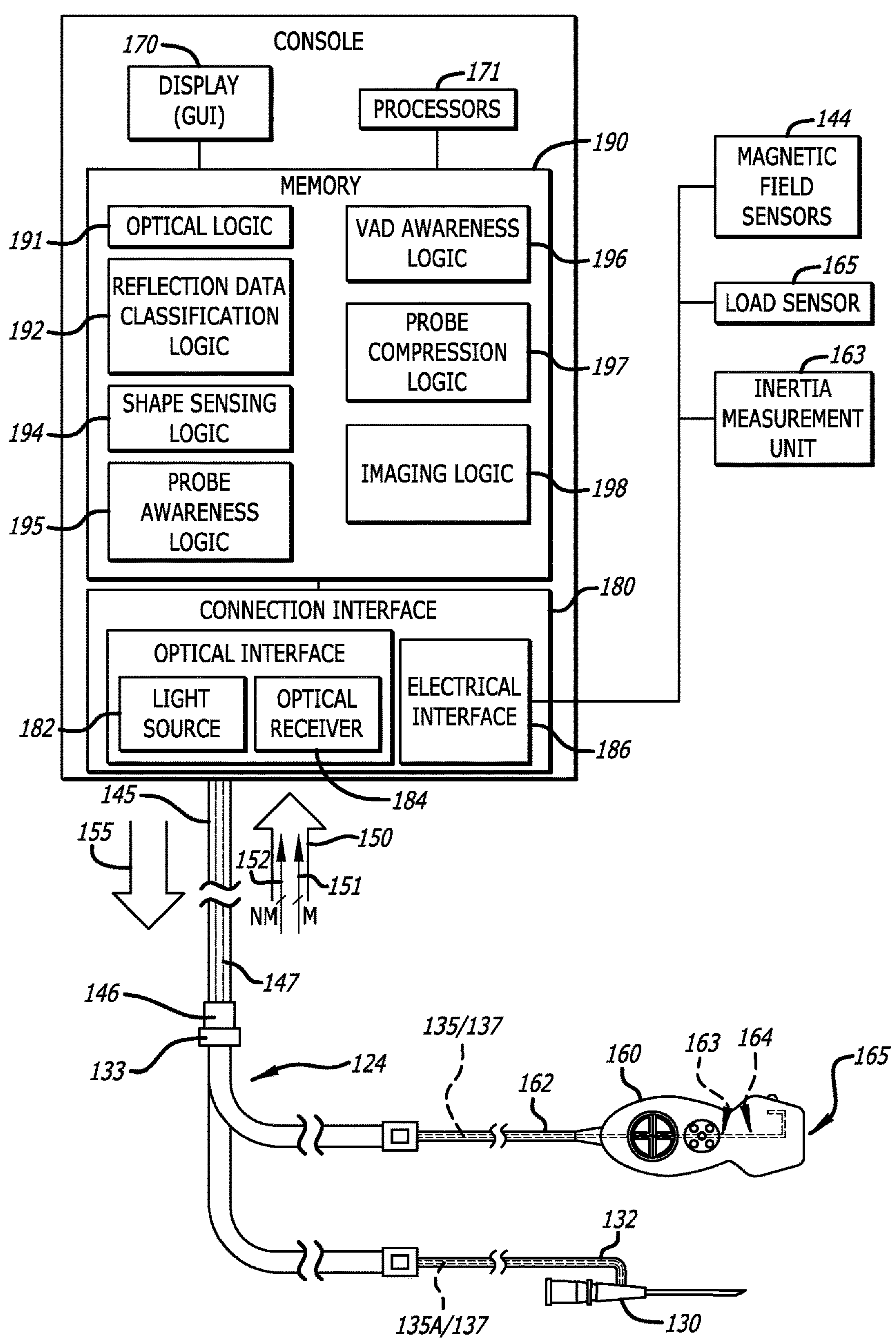
FIG. 1B is a block diagram of a console of the ultrasound training system of FIG. 1A coupled with various components of the ultrasound training system, in accordance with some embodiments.

FIG. 1B illustrates a console 110 of the system module 105 including interactions with various components of the system 100. According to one embodiment, the console 110 includes one or more processors 171, a memory 190, and a display 170, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Pat. No. 10,992,078, the entire contents of which are incorporated by reference herein. The one or more processors 171, with access to the memory 190 (e.g., non-volatile memory or non-transitory, computer-readable medium), are included to control functionality of the system 100 during operation. The display 170 may be a liquid crystal diode (LCD) display integrated into the console 110 and employed as a user interface to display information to the clinician, especially during an instrument placement procedure. In another embodiment, the display 170 may be separate from the console 110. Although not shown, a user interface is configured to provide user control of the system 100.

The memory 190 includes logic modules, such as optical logic 191, reflection classification logic 192, shape sensing logic 194, probe awareness logic 195, VAD awareness logic 196, probe compression logic 197, and imaging logic 198. Each of the logic modules are further described below.

The console further includes a connection interface 180 which include an electrical interface 186 to facilitate electrical connections between the console 110 and the magnetic field sensors 144, the load sensor 165, and the IMU 163. In some embodiments, the connection interface 180 may also include a light source 182 and an optical receiver 184 to facilitate optical communication with one or more optical fibers.

According to the illustrated embodiment, the content depicted by the display 170 may constitute a two-dimensional or three-dimensional representation of the physical state (e.g., length, shape, form, and/or orientation) of the probe 160 computed from characteristics of reflected light signals 150 returned to the console 110. The reflected light signals 150 constitute light of a specific spectral width of broadband incident light 155 reflected back to the console 110. According to one embodiment of the disclosure, the reflected light signals 150 may pertain to various discrete portions (e.g., specific spectral widths) of broadband incident light 155 transmitted from and sourced by the optical logic 191, as described below.

According to some embodiments, the probe 160 may include an optical fiber 135 extending between the probe 160 and the system module 105 via the probe cable 162. Similarly, in some embodiments, the VAD 130 may include an optical fiber 135A extending between the VAD 130 and the system module 105 via the VAD cable 132.

The console connector 133 enables the optical fiber 135 and in some embodiments, the optical fiber 135A, to be operably connected to the console 110 via an interconnect 145 including one or more optical fibers 137 (hereinafter, "optical fiber(s)") terminated by a single optical connector 146 (or terminated by dual connectors). Herein, the connector 146 is configured to engage (mate) with the console connector 133 to allow for the propagation of light between the console 110 and the probe 160.

Referring still to FIG. 1B, the optical logic 191 is configured to support spatial awareness of the probe 160, which may be used to determine the physical state associated with the probe 160. The physical state of the probe 160 may be based on changes in characteristics of the reflected light signals 150 received at the console 110 from the optical fiber 135 extending along the probe cable 162 to the probe 160. The characteristics may include shifts in wavelength caused by strain on certain regions of the core fibers integrated within the optical fiber core 135 positioned along the probe cable 162 and within the probe 160, as shown below. As discussed herein, the optical fiber core 135 may comprise core fibers $\mathbf{137}_1$-$\mathbf{137}_M$ (M=1 for a single core, and M>2 for a multi-core), where the core fibers $\mathbf{137}_1$-$\mathbf{137}_M$ may collectively be referred to as core fiber(s) 137. Unless otherwise specified or the instant embodiment requires an alternative interpretation, embodiments discussed herein will refer to a multi-core optical fiber 135. From information associated with the reflected light signals 150, the console 110 may determine (through computation or extrapolation of the wavelength shifts) the physical state of the probe 160.

The light source 182 and an optical receiver 184 are configured to provide light to and receive light from the optical fiber 135. The light source 182 is configured to transmit the incident light 155 (e.g., broadband) for propagation over the optical fiber(s) 147 included in the interconnect 145, which are optically connected to the multi-core optical fiber core 135 positioned along the probe cable 162 and within the probe 160. In one embodiment, the light source 182 is a tunable swept laser, although other suitable light sources can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the multi-core optical fiber 135 and (ii) translate the reflected light signals 150 into reflection data, namely data in the form of electrical signals representative of the reflected light signals including wavelength shifts caused by strain of the optical fiber 135. The reflected light signals 150 associated with different spectral widths may include reflected light signals 151 provided from sensors positioned in the center core fiber (reference) of the multi-core optical fiber 135 and reflected light signals 152 provided from sensors positioned in the periphery core fibers of the multi-core optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the one or more processors 171, which governs their operation. Also, the optical receiver 184 is operably coupled to provide the reflection data to the memory 190 for storage and processing by reflection data classification logic 192. The reflection data classification logic 192 may be configured to (i) identify which core fibers pertain to which of the received reflection data and (ii) segregate the reflection data stored within the memory 190 provided from reflected light signals 150 pertaining to similar regions of the probe 160 or spectral widths into analysis groups. The reflection data for each analysis group is made available to shape sensing logic 194 for analytics.

According to one embodiment of the disclosure, the shape sensing logic 194 is configured to compare wavelength shifts measured by sensors deployed in each periphery core fiber at the same measurement region of the probe cable 162 (including the same spectral width) to the wavelength shift at a center core fiber of the multi-core optical fiber 135 positioned along the central axis and operating as a neutral axis of bending. From these analytics, the shape sensing logic 194 may determine the shape the core fibers have taken in three-dimensional space and may further determine the current physical state (e.g., position and orientation) of the probe 160 in three-dimensional space.

Similarly, in some embodiments, the 132 extending between the VAD and the console may include an optical fiber 135A that may in some respects resemble the components, features and functionality of the optical 135 described above. Accordingly, the relevant descriptions of such features and functionality of the probe 160 and the associated probe cable 162 may in some respects apply to the features and functionality of the VAD 130 and the associated VAD cable 132. Any suitable combination of the optically enabled features, and variations of the same, described with respect to the probe 160 can be employed with the VAD 130.

By way of summary, the optical fibers 135 and 135A may enable the system 100 to define (i.e., know) a spatial awareness of the probe 160 and the VAD 130 in 3D space and/or with respect to each other. In the illustrated embodiment, system 100 generally includes both the probe 160 and the VAD 130. However, in some embodiments, the probe 160 and the associated probe cable 162 may omit the optical fiber 135 and the optical features and functionality enabled by the optical fiber 135. Similarly, the VAD 130 may omit the VAD cable 132 and the optical features and functionality enabled by the optical fiber 135A.

The ultrasound imaging probe 160 is operatively connected to the console 110 via electrical wires extending along the probe cable 162.

Figure 2:
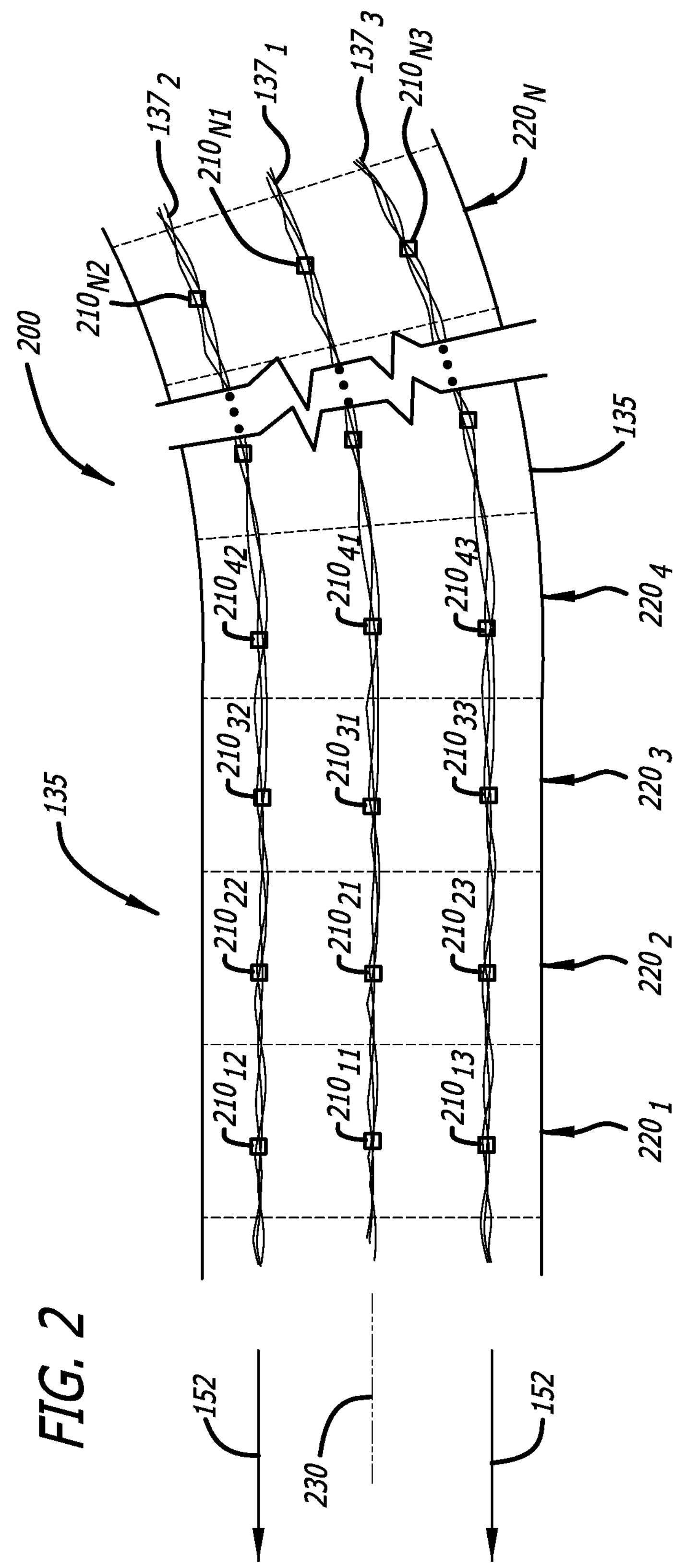
FIG. 2 is an exemplary embodiment of a structure of a section of the multi-core optical fiber coupled between a probe and system module of the ultrasound training system of FIG. 1A, in accordance with some embodiments.

FIG. 2, illustrates an exemplary embodiment of a structure of a section of the multi-core optical fiber 135 extending along the probe cable 162 and within the probe 160 of FIG. 1A, which structure may also apply to the multi-core optical fiber 135A, in accordance with some embodiments. The multi-core optical fiber section 200 of the multi-core optical fiber 135 depicts certain core fibers $\mathbf{137}_1$-$\mathbf{137}_M$ (M≥2, M=4 as shown, see FIG. 3) along with the spatial relationship between sensors (e.g., reflective gratings) $\mathbf{210}_{11}$-$\mathbf{210}_{NM}$ (N≥2; M≥2) present within the core fibers $\mathbf{137}_1$-$\mathbf{137}_M$, respectively. As noted above, the core fibers $\mathbf{137}_1$-$\mathbf{137}_M$ may be collectively referred to as "the core fibers 137."

Figure 4:
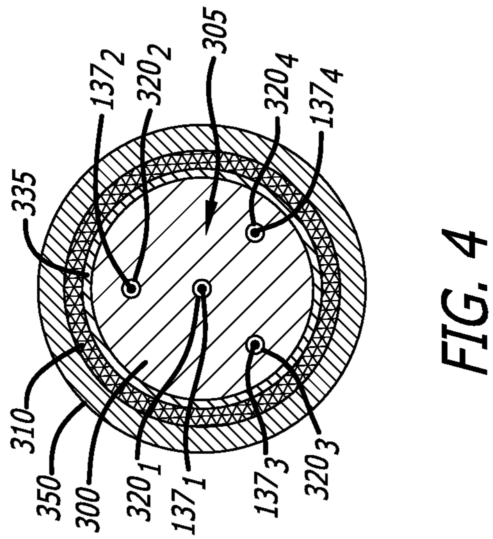
FIG. 4 is a cross-sectional view of the optical fiber of FIG. 3, in accordance with some embodiments.
Figure 3:
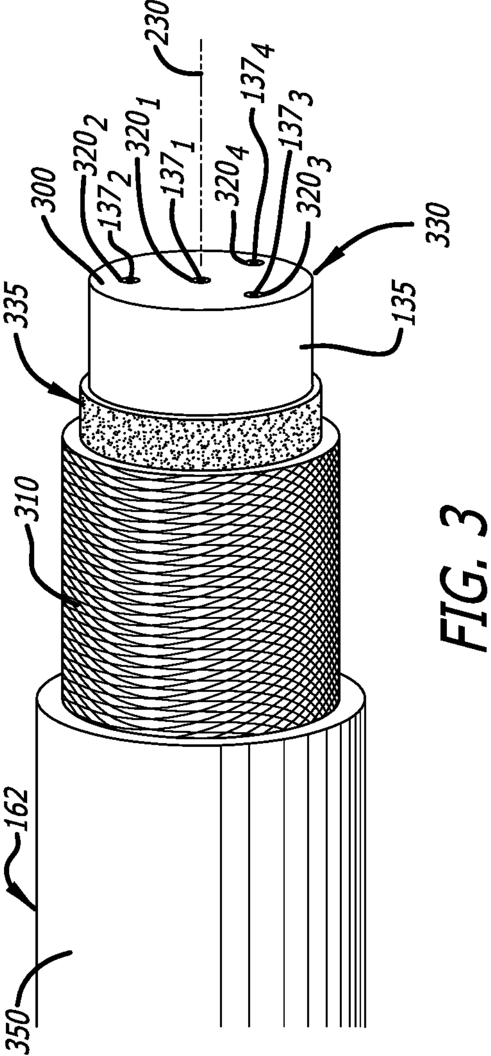
FIG. 3 is a first exemplary embodiment of the optical fiber of FIGS. 1A-1B, in accordance with some embodiments.

As shown, the section 200 is subdivided into a plurality of cross-sectional regions $\mathbf{220}_1$-$\mathbf{220}_N$, where each cross-sectional region $\mathbf{220}_1$-$\mathbf{220}_N$ corresponds to reflective gratings $\mathbf{210}_{11}$-$\mathbf{210}_{14}$ . . . $\mathbf{210}_{N1}$-$\mathbf{210}_{N4}$. Some or all of the cross-sectional regions $\mathbf{220}_1$ . . . $\mathbf{220}_N$ may be static (e.g., prescribed length) or may be dynamic (e.g., vary in size among the regions $\mathbf{220}_1$ . . . $\mathbf{220}_N$). A first core fiber $\mathbf{137}_1$ is positioned substantially along a center (neutral) axis 230 while core fiber $\mathbf{137}_2$ may be oriented within the cladding of the multi-core optical fiber 135, from a cross-sectional, front-facing perspective, to be position on "top" the first core fiber $\mathbf{137}_1$. In this deployment, the core fibers $\mathbf{137}_3$ and $\mathbf{137}_4$ may be positioned "bottom left" and "bottom right" of the first core fiber $\mathbf{137}_1$. As examples, FIGS. 3-4 provide illustrations of such.

Referencing the first core fiber $\mathbf{137}_1$ as an illustrative example, when the probe 160 and the probe cable 162 are operative, each of the reflective gratings $\mathbf{210}_1$-$\mathbf{210}_N$ reflects light for a different spectral width. As shown, each of the gratings $\mathbf{210}_{1i}$-$\mathbf{210}_{Ni}$ (1≤i≤M) is associated with a different, specific spectral width, which would be represented by different center frequencies of $f_1$ . . . $f_N$, where neighboring spectral widths reflected by neighboring gratings are non-overlapping according to one embodiment of the disclosure.

Herein, positioned in different core fibers $\mathbf{137}_2$-$\mathbf{137}_3$ but along at the same cross-sectional regions 220-$\mathbf{220}_N$ of the multi-core optical fiber 135, the gratings $\mathbf{210}_{12}$-$\mathbf{210}_{N2}$ and $\mathbf{210}_{13}$-$\mathbf{210}_{N3}$ are configured to reflect incoming light at same (or substantially similar) center frequency. As a result, the reflected light returns information that allows for a determination of the physical state of the optical fibers 137 (and the probe 160 and or the elongate member 125) based on wavelength shifts measured from the returned, reflected light. In particular, strain (e.g., compression or tension) applied to the multi-core optical fiber 135 (e.g., at least core fibers $\mathbf{137}_2$-$\mathbf{137}_3$) results in wavelength shifts associated with the returned, reflected light. Based on different locations, the core fibers $\mathbf{137}_1$-$\mathbf{137}_4$ experience different types and degrees of strain based on shape of the optical fiber 135 extending along the probe cable 162 and within the probe 162. The strain may bending strain as illustrated in FIG. 2 or torsional strain as may result when the probe 160 is rotated.

For example, with respect to the multi-core optical fiber section 200 of FIG. 2, in response to angular (e.g., radial) movement of the probe 160 is in the left-veering direction, the fourth core fiber $\mathbf{137}_4$ (see FIG. 3) of the multi-core optical fiber 135 with the shortest radius during movement (e.g., core fiber closest to a direction of angular change) would exhibit compression (e.g., forces to shorten length). At the same time, the third core fiber $\mathbf{137}_3$ with the longest radius during movement (e.g., core fiber furthest from the direction of angular change) would exhibit tension (e.g., forces to increase length). As these forces are different and unequal, the reflected light from reflective gratings $\mathbf{210}_{N2}$ and $\mathbf{210}_{N3}$ associated with the core fiber $\mathbf{137}_2$ and $\mathbf{137}_3$ will exhibit different changes in wavelength. The differences in wavelength shift of the reflected light signals 150 can be used to extrapolate the physical configuration of the probe cable 162 and probe 160 by determining the degrees of wavelength change caused by compression/tension for each of the periphery fibers (e.g., the second core fiber $\mathbf{137}_2$ and the third core fiber $\mathbf{137}_3$) in comparison to the wavelength of the reference core fiber (e.g., first core fiber $\mathbf{137}_1$) located along the neutral axis 230 of the multi-core optical fiber 135. These degrees of wavelength change may be used to extrapolate the physical state (position and orientation) of the probe 160. The reflected light signals 150 are reflected back to the console 110 via individual paths over a particular core fiber 137*i*-$\mathbf{137}_M$.

Referring to FIG. 3, a first exemplary embodiment of the probe cable 162 supporting optical signaling is shown in accordance with some embodiments. The probe cable 162 may also include electrical wires (not shown) to facilitate an electrical connection between the probe 160 and the system module 105. Herein, the probe cable 162 features a centrally located multi-core optical fiber 135, which includes a cladding 300 and a plurality of core fibers $\mathbf{137}_1$-$\mathbf{137}_M$ (M≥2; M=4) residing within a corresponding plurality of lumens $\mathbf{320}_1$-$\mathbf{320}_M$. While the multi-core optical fiber 135 is illustrated within four (4) core fibers $\mathbf{137}_1$-$\mathbf{137}_4$, a greater number of core fibers $\mathbf{137}_1$-$\mathbf{137}_M$ (M>4) may be deployed to provide a more detailed three-dimensional sensing of the physical state (e.g., shape, etc.) of the multi-core optical fiber 135 and the probe cable 162 deploying the optical fiber 135.

In some embodiments, the multi-core optical fiber 135 may be encapsulated within a concentric braided tubing 310 positioned over a low coefficient of friction layer 335. The braided tubing 310 may feature a "mesh" construction, in which the spacing between the intersecting conductive elements is selected based on the degree of rigidity desired for the probe cable 162, as a greater spacing may provide a lesser rigidity, and thereby, a more pliable probe cable 162.

According to this embodiment of the disclosure, as shown in FIGS. 3-4, the core fibers $\mathbf{137}_1$-$\mathbf{137}_4$ include (i) a central core fiber $\mathbf{137}_1$ and (ii) a plurality of periphery core fibers $\mathbf{137}_2$-$\mathbf{137}_4$, which are maintained within lumens $\mathbf{320}_1$-$\mathbf{320}_4$ formed in the cladding 300. According to one embodiment of the disclosure, one or more of the lumens $\mathbf{320}_1$-$\mathbf{320}_4$ may be configured with a diameter sized to be greater than the diameter of the core fibers $\mathbf{137}_1$-$\mathbf{137}_4$. By avoiding a majority of the surface area of the core fibers $\mathbf{137}_1$-$\mathbf{137}_4$ from being in direct physical contact with a wall surface of the lumens $\mathbf{320}_1$-$\mathbf{320}_4$, the wavelength changes to the incident light are caused by angular deviations in the multi-core optical fiber 135 thereby reducing influence of compression and tension forces being applied to the walls of the lumens $\mathbf{320}_1$-$\mathbf{320}_M$, not the core fibers $\mathbf{137}_1$-$\mathbf{137}_M$ themselves.

As further shown in FIGS. 3-4, the core fibers $\mathbf{137}_1$-$\mathbf{137}_4$ may include central core fiber $\mathbf{137}_1$ residing within a first lumen $\mathbf{320}_1$ formed along the first neutral axis 230 and a plurality of core fibers $\mathbf{137}_2$-$\mathbf{137}_4$ residing within lumens $\mathbf{320}_2$-$\mathbf{320}_4$ each formed within different areas of the cladding 300 radiating from the first neutral axis 230. In general, the core fibers $137_2$-$137_4$, exclusive of the central core fiber $137_1$, may be positioned at different areas within a cross-sectional area 305 of the cladding 300 to provide sufficient separation to enable three-dimensional sensing of the multi-core optical fiber 135 based on changes in wavelength of incident light propagating through the core fibers $137_2$-$137_4$ and reflected back to the console for analysis.

For example, where the cladding 300 features a circular cross-sectional area 305 as shown in FIG. 4, the core fibers $137_2$-$137_4$ may be positioned substantially equidistant from each other as measured along a perimeter of the cladding 300, such as at “top” (12 o’clock), “bottom-left” (8 o’clock) and “bottom-right” (4 o’clock) locations as shown. Hence, in general terms, the core fibers $137_2$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape.

Referring still to FIGS. 3-4, the braided tubing 310 provides mechanical integrity to the multi-core optical fiber 135. The cladding 300 and the braided tubing 310, which is positioned concentrically surrounding a circumference of the cladding 300, are contained within an outer layer 350. The outer layer 350 may be a sheath or conduit made of protective material that encapsulates both for the cladding 300 and the braided tubing 310, as shown.

The shape of the optical fiber 135 in three-dimensional space may be translated into a 3D shape of the probe cable 162. As the dimensions of the probe cable 162 (e.g., diameter and length) along a measured region may be known, the spatial relationship of defined segments along the measured region may be calculated according to established engineering mathematical formulas that relate strain to a radius of curvature. In other words, the position in 3D space of a first point located along the measured region with respect to a second point located along the measured region may be calculated. Similarly, the 3D direction of a first unit vector defining the direction of the cable 162 at the first point with respect to the direction of a second unit vector defining the direction of the probe 160 at the second point may be calculated. By way of summary, the position and direction of the cable 162 at any point with respect to the position and direction of the cable 162 at any other point may be calculated. As such, the position and orientation of the probe 160 may be calculated or otherwise determined.

Figure 5A:
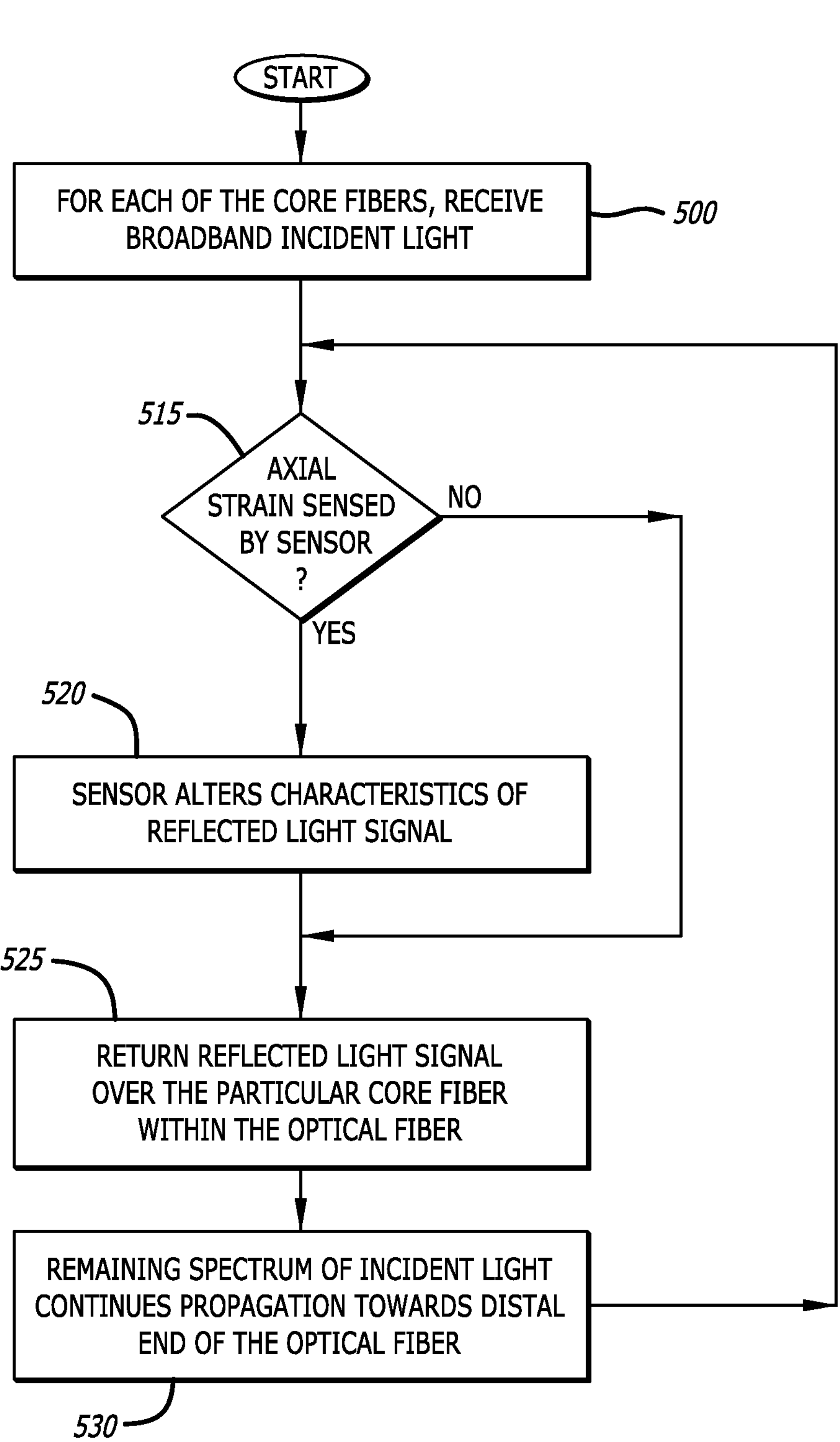
FIGS. 5A-5B are flowcharts of the methods of operations conducted by the ultrasound training system of FIG. 1A to achieve optic 3D shape sensing of the optical fiber, in accordance with some embodiments.
Figure 5B:
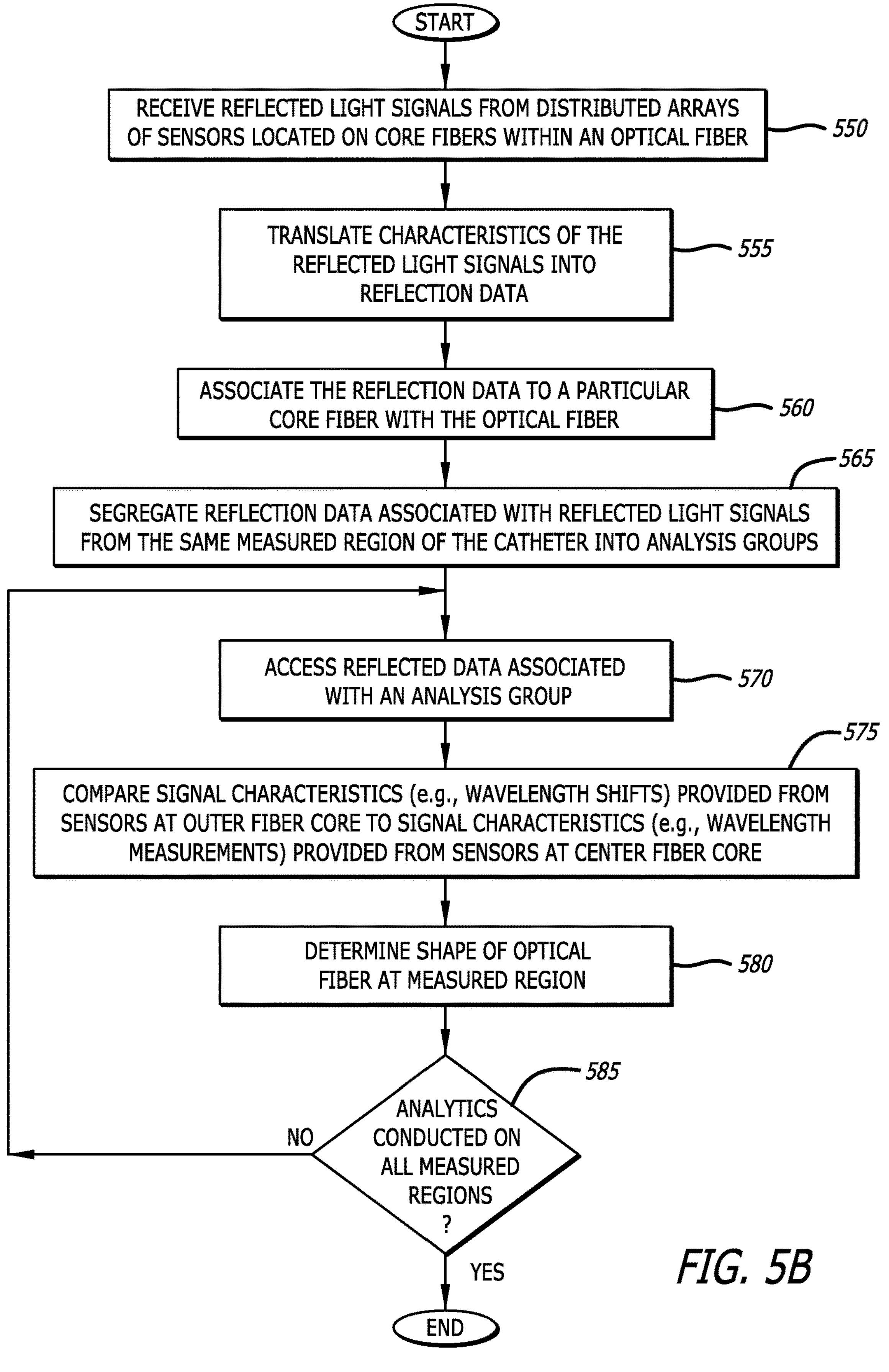

Referring to FIGS. 5A-5B, flowcharts of methods of operations conducted by the system 100 of FIG. 1A to achieve optic 3D shape sensing are shown in accordance with some embodiments. Each core fiber includes a plurality of sensors spatially distributed along its length between at least the proximal and distal ends of the optical fiber 135. This array of sensors is distributed to position sensors at different regions of the core fiber to enable distributed measurements of strain throughout the entire length or a selected portion of the optical fiber 135. These distributed measurements may be conveyed through reflected light of different spectral widths (e.g., specific wavelength or specific wavelength ranges) that undergoes certain wavelength shifts based on the type and degree of strain.

According to one embodiment of the disclosure, as shown in FIG. 5A, for each core fiber, broadband incident light is supplied to propagate through a particular core fiber (block 500). The incident light upon reaching a sensor of a distributed array of sensors measuring strain on a particular core fiber, light of a prescribed spectral width associated with the first sensor is be reflected back to an optical receiver within a console. Herein, the sensor alters characteristics of the reflected light signal to identify the type and degree of strain on the particular core fiber as measured by the first sensor (blocks 515-520). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the optical fiber (blocks 525-530). The remaining spectrum of the incident light may encounter other sensors of the distributed array of sensors, where each of these sensors would operate as set forth in blocks 505-530 until the last sensor of the distributed array of sensors returns the reflected light signal associated with its assigned spectral width and the remaining spectrum is discharged as illumination.

Referring now to FIG. 5B, during operation, multiple reflected light signals are returned to the console from each of the plurality of core fibers residing within the corresponding plurality of micro-lumens formed within the optical fiber. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 550-555). The reflection data classification logic 192 is configured to identify which core fibers pertain to which reflection data and segregate reflection data provided from reflected light signals pertaining to a particular measurement region (or similar spectral width) into analysis groups (block 560-565).

Each analysis group of reflection data is provided to shape sensing logic for analytics (block 570). Herein, the shape sensing logic compares wavelength shifts at each outer core fiber with the wavelength shift at the center core fiber positioned along central axis and operating as a neutral axis of bending (block 575). From these analytics, on all analytic groups (e.g., reflected light signals from sensors in all or most of the core fibers), the shape sensing logic may determine the shape the core fibers have taken in three-dimensional space, from which the shape sensing logic can determine the current physical state of the optical fiber in three-dimension space (blocks 580-585).

Figure 6:
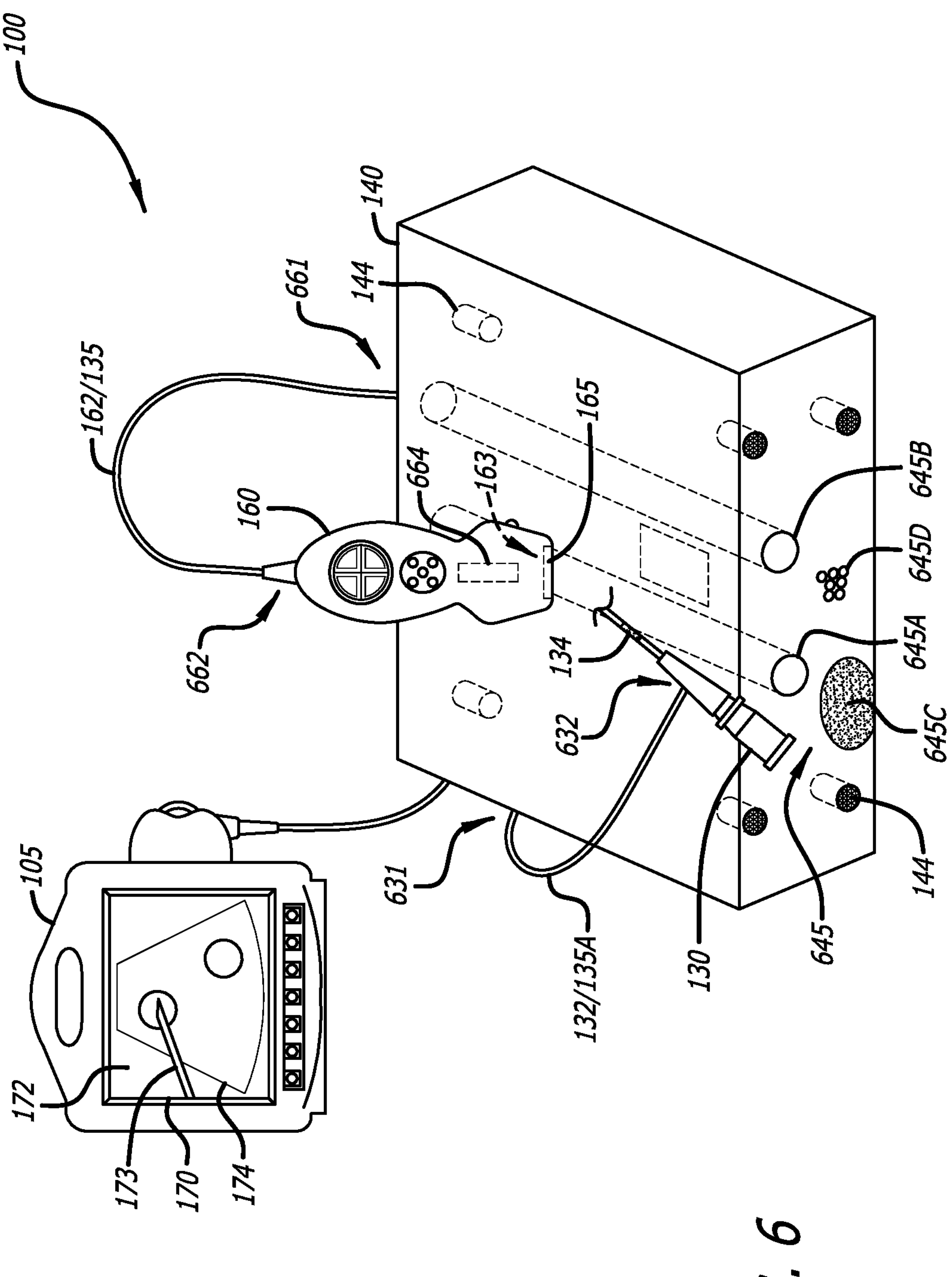
FIG. 6 illustrates an exemplary embodiment of the ultrasound training system of FIGS. 1A-1B according to various implementations of the ultrasound training system during use, in accordance with some embodiments.

FIG. 6 illustrates the system 100 during a training instance representing the insertion of a needle into a vein of a patient according to various implementations. Shown in FIG. 6 are the system module 105 operatively coupled with the patient simulation block 140. The probe 160 is also operatively coupled with the system module 105 via the patient simulation block 140. The VAD 130 is shown inserted into the patient simulation block 140. The simulated image 172 is depicted on the display 170 showing the simulated ultrasound image 174 having the simulated VAD image 173 overlayed thereon.

In some embodiments, the patient simulation block 140 may include a number of anatomic elements 654, such as a vein 645A, an artery 645B, a bone 645C and a bundle of nerves 645D, for example. Each of the vein 645A and the artery 645B may include a lumen extending through the patient simulation block 140 configured for receiving the VAD 130 therein. The patient simulation block 140 may be composed of a material that has physical properties similar to body tissue so that physical interaction of the probe 160 with the patient simulation block 140 is similar to a physical interaction of a typical ultrasound probe with a patient. Furthermore, the one or more of anatomic elements 654 may be composed of materials that have physical properties similar to corresponding anatomic elements of the patient. For example, the bone 645C may be composed of a material that is harder than the patient simulation block 140 generally. In other embodiments, the patient simulation block 140 may omit any or all of the exemplary anatomical elements 645.

The patient simulation block 140 includes a number (e.g., 1, 2, 3, or more) magnetic field sensors 144 physically coupled with the patient simulation block 140. In some embodiments, the magnetic field sensors 144 may be incorporated into the patient simulation block 140. In other embodiments, the magnetic field sensors 144 may be attached to an outside surface of the patient simulation block 140 or otherwise secured at defined locations with respect to the patient simulation block 140. The magnetic field sensors 144 are operatively coupled the system module 105 via a wired connection.

In some embodiments, the probe 160 may include at least one magnetic element 664 (e.g., a magnet) configured to define a probe magnetic field that is detectable by at least a first subset of the magnetic field sensors 144 such that the electrical data/signals transmitted to the system module 105 by the magnetic field sensors 144 may be processed by the probe awareness logic 195 to determine a position and an orientation of the probe 160 with respect to the patient simulation block 140.

In some embodiments, the probe 160 includes the IMU 163 configured to provide electrical signals/data related to movement and/or rotation of the probe 160. In such embodiments, the probe awareness logic 195 may combine the electrical signals/data from the first subset of the magnetic field sensors 144 related to the probe magnetic field with the electrical signals/data from the IMU 163 to further determine the position and the orientation of the probe 160 with respect to the patient simulation block 140.

FIG. 6 further illustrates the VAD 130 having a cannula inserted into the patient simulation block 140. The VAD 130 includes at least one magnetic element 134 (e.g., a magnet) configured to define a VAD magnetic field that is detectable by at least a second subset of the magnetic field sensors 144 such that the electrical data/signals transmitted to the system module 105 by the magnetic field sensors 144 may be processed by the VAD awareness logic 196 to determine a position and an orientation of the VAD 130 with respect to the patient simulation block 140 and/or with respect to at least one of the anatomical elements 645. In some embodiments, the second subset of the magnetic field sensors 144 may (i) be different that the first subset of the magnetic field sensors 144, (ii) overlap the first subset of the magnetic field sensors 144, or (iii) be the same as first subset of the magnetic field sensors 144.

In other embodiments, electrical data/signals transmitted to the system module 105 by the magnetic field sensors 144 may be processed by VAD awareness logic 196 to determine a position and an orientation of the VAD 130 with respect to the probe 160. In such embodiments, magnetic element 664 may be replaced by the magnetic field sensors so that the probe 160 provides electrical data/signals to the system module 105 that may be processed by the VAD awareness logic 196 to determine the position and the orientation of the VAD 130 with respect to the probe 160 directly.

In some implementations, the probe cable 162 may include the optical fiber 135 extending between the probe 160 and the patient simulation block 140. More specifically, the optical fiber 135 may be coupled with the patient simulation block 140 so that a first end 661 of the optical fiber 135 positionally and rotationally fixed with respect to the patient simulation block 140. Similarly, the optical fiber 135 may be coupled with the patient probe 160 so that a second end 662 of the optical fiber 135 is positionally and rotationally fixed with respect to the probe 160. As such, the probe awareness logic 195 may process shape sensing data of the shape sensing logic 194 to determine the position and the orientation of the probe 160 with respect to the patient simulation block 140.

In some implementations, the probe awareness logic 195 may be configured to determine the position and orientation of the probe 160 via only the magnetic element 664 and the corresponding the magnet field sensors 144. In some implementations, the probe awareness logic 195 may be configured to determine the position and orientation of the probe 160 via the magnetic element 664 and the corresponding the magnet field sensors 144 in combination with the IMU 163.

In some implementations, the probe awareness logic 195 may be configured to determine the position and orientation of the probe 160 via only the optical fiber 135. In some implementations, the probe awareness logic 195 may be configured to determine the position and orientation of the probe 160 via the optical fiber 135 in combination with the IMU 163. In some implementations, the probe awareness logic 195 may be configured to determine the position and orientation of the probe 160 via the optical fiber 135 in combination with the magnetic element 664 and the corresponding the magnet field sensors 144. In some implementations, the probe awareness logic 195 may be configured to determine the position and orientation of the probe 160 via the optical fiber 135 in combination with the magnetic element 664 and the corresponding the magnet field sensors 144 and in further combination with the IMU 163.

In some implementations, the VAD cable 132 may include the optical fiber 135A extending between the VAD 130 and the patient simulation block 140. More specifically, the optical fiber 135A may be coupled with the patient simulation block 140 so that a first end 631 of the optical fiber 135A positionally and rotationally fixed with respect to the patient simulation block 140. Similarly, the optical fiber 135A may be coupled with the patient VAD 130 so that a second end 632 of the optical fiber 135A is positionally and rotationally fixed with respect to the VAD 130. As such, the VAD awareness logic 196 may process shape sensing data of the shape sensing logic 194 to determine the position and the orientation of the VAD 130 with respect to the patient simulation block 140.

In some implementations, the VAD awareness logic 196 may be configured to determine the position and orientation of the VAD 130 via only the magnetic elements 662 and the corresponding the magnet field sensors 144. In some implementations, the VAD awareness logic 196 may be configured to determine the position and orientation of the VAD 130 via only the optical fiber 135A. In some implementations, the VAD awareness logic 196 may be configured to determine the position and orientation of the VAD via the optical fiber 135A in combination with the magnetic element 662 and the corresponding magnet field sensors 144.

In some implementations, the probe 160 may include the load sensor 165 communicatively coupled with the system module, where the load sensor 165 determines the compressive load magnitude applied to the patient simulation block 140 by the trainee. In some instances of ultrasound imaging, the compressive load applied to a patient may alter the shape or position of the anatomical elements of the patient. For example, in some instances, the compressive load may flatten the cross-section of a vein of the patient. In one implementation, the vein 645A may be crushed or partially crushed by the compressive force of the probe 160 during use. As such, the probe compression logic 197 may process electrical signals/data from the load sensor 165 to determine the compressive load magnitude and relate the compressive load magnitude to an altered cross-sectional shape of the vein 645A or any other of the anatomical elements 645. As stated above, in some implementations, the anatomical elements 645 may be omitted from the patient simulation block 140. In such an implementation, the probe compression logic 197 may process electrical signals/data from the load sensor 165 to determine the compressive load magnitude and relate the compressive load magnitude to an altered cross-sectional shape of computer generated vein or any other computer generated anatomical element.

The imaging logic 198 is generally configured to depict the simulated image 172 on the display 170 which may be a live image. In some implementations, the simulated image 172 includes the simulated VAD image 173 overlayed atop the simulated ultrasound image 174. The simulated ultrasound image 174 may be a computer generated image representing an exemplary ultrasound image of a patient, i.e., an image that a clinician may observe during an actual ultrasound imaging procedure and as such, the simulated ultrasound image 174 may include a number of simulated anatomical elements (e.g., blood vessels). The simulated ultrasound image 174 may be correlated with the position and orientation of the probe 160 with respect to the patient simulation block 140, i.e., the simulated ultrasound image 174 may change as the trainee moves or orients the probe 160. In some implementations, the depicting of the simulated ultrasound image 174 may be initiated by contact of the probe 160 with the patient simulation block 140 as detected by the load sensor 165.

In some implementations, the simulated ultrasound image 174 may be correlated with the location of one or more of the artificial anatomical elements 645 within the patient simulation block 140. In other words, the position and orientation of the simulated anatomical elements in the simulated ultrasound image 174 may be correlated with the position and orientation of the probe 160 with respect to the artificial anatomical elements 645 within the patient simulation block 140. In further implementations, the simulated ultrasound image 174 may be an actual ultrasound image of the patient simulation block 140 including the artificial anatomical elements 645.

The imaging logic 198 may depict the simulated VAD image 173 atop the simulated ultrasound image 174 so that the position and the orientation of the VAD 130 is correlated with the position and the orientation of the probe 160. More specifically, the imaging logic 198 may overlay the simulated VAD image 173 atop the simulated ultrasound image 174 based on the position and orientation of the probe 160 as determined by the probe awareness logic 195 and the position and orientation of the VAD 130 as determined by the VAD awareness logic 196. In some implementations, the imaging logic 198 define the type and/or size of the simulated VAD image 173 based on a magnetic signature of the VAD 130.

In some implementations, the imaging logic 198 may depict the simulated ultrasound image 174 showing one or more anatomical elements having a shape altered by the compressive load. More specifically, the imaging logic 198 may receive compression load data from the probe compression logic 197, and based on the compression load data, depict at least one anatomical element having an altered shape, such as a blood vessel having a crushed shape, for example.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound training system comprising:
- an ultrasound probe;
- a patient simulation block configured for engagement with the ultrasound probe, the ultrasound probe including a load sensor configured to determine a compression force magnitude between the ultrasound probe and the patient simulation block; and
- a system module coupled with the ultrasound probe, the system module including a console having a number of processors and a non-transitory computer readable medium having logic stored thereon that when executed by the processors performs operations including:
  - obtaining a position and an orientation of the ultrasound probe with respect to the patient simulation block;
  - depicting a simulated ultrasound image of one or more anatomical elements on a display of the ultrasound training system based on the position and the orientation of the ultrasound probe; and
  - adjusting a shape of the one or more anatomical elements depicted in the simulated ultrasound image based on the compression force magnitude.

2. The system of claim 1, wherein the operations further include dynamically adjusting the simulated ultrasound image based on at least one of dynamic repositioning or dynamic reorienting of the ultrasound probe.

3. The system of claim 1, wherein the one or more anatomical elements include a blood vessel.

4. The system of claim 1, further comprising a vascular access device (VAD) operatively coupled with the system module, the VAD configured for positioning and orienting by a trainee with respect to the patient simulation block, wherein the operations further include:
- obtaining a position and an orientation of the VAD with respect to the patient simulation block; and
- overlaying a simulated image of the VAD atop the simulated ultrasound image.

5. The system of claim 4, wherein the operations further include dynamically adjusting the simulated image of the VAD based on at least one of dynamic repositioning or dynamic reorienting of the VAD.

6. The system of claim 4, further comprising a plurality of magnetic field sensors operatively coupled with the system module, wherein obtaining the position and the orientation of the ultrasound probe includes determining a position and an orientation of one or more magnetic elements of the ultrasound probe via the plurality of magnetic field sensors.

7. The system of claim 6, wherein obtaining the position and the orientation of the VAD includes determining a position and an orientation of the one or more magnetic elements of the VAD via the plurality of magnetic field sensors.

8. The system of claim 7, wherein:

the one or more magnetic elements of the VAD define a magnetic signature of the VAD, and the operations further include defining at least one of a type or a size of the VAD depicted in a simulated image of the VAD based on the magnetic signature.

9. The system of claim 6, wherein the plurality of magnetic field sensors are physically coupled with the patient simulation block.

10. The system of claim 4, wherein:

the patient simulation block includes one or more artificial anatomic elements disposed therein, and operations further include aligning the one or more anatomical elements of a computer generated image with the one or more artificial anatomic elements.

11. The system of claim 10, wherein:

the patient simulation block is configured to receive the VAD inserted therein including insertion within at least one of the one or more artificial anatomic elements, and overlaying the simulated image of the VAD atop the simulated ultrasound image includes depicting the VAD inserted within at least one of the one or more anatomical elements aligned with the at least one of the one or more artificial anatomic elements.

12. The system of claim 11, wherein:

the ultrasound probe is configured to obtain an actual ultrasound image of the patient simulation block including the one or more artificial anatomic elements, and the simulated ultrasound image includes the actual ultrasound image of the patient simulation block.

13. The system of claim 12, wherein the simulated ultrasound image includes a combination of:

the actual ultrasound image of the patient simulation block; and a computer generated image of the one or more anatomical elements.

14. The system of claim 1, wherein:

the ultrasound probe includes an inertial measurement unit (IMU) operatively coupled with the system module, and obtaining the position and the orientation of the ultrasound probe further includes determining at least one of the position or the orientation of the ultrasound probe based on data received from the IMU.

15. The system of claim 1, further comprising a first optical fiber coupled between the system module and the ultrasound probe, wherein:

the first optical fiber includes one or more core fibers including a plurality of sensors distributed along a longitudinal length of a corresponding core fiber and each sensor of the plurality of sensors being configured to (i) reflect a light signal of a different spectral width based on received incident light, and (ii) change a characteristic of the reflected light signal based on a shape of the first optical fiber, and the operations further include:

providing an incident light signal to the first optical fiber;

receiving reflected light signals of different spectral widths of the received incident light from one or more of the plurality of sensors;

processing the reflected light signals associated with the one or more of core fibers to determine a three-dimensional (3D) shape of the first optical fiber.

16. The system of claim 15, wherein:

the first optical fiber is (i) physically coupled with the ultrasound probe at a first end of the first optical fiber and (ii) physically coupled with the patient simulation block at a second end of the first optical fiber, and obtaining the position and the orientation of the ultrasound probe with respect to the patient simulation block includes determining the position and the orientation based on the shape of the first optical fiber.

17. The system of claim 15, further comprising a second optical fiber coupled between the system module and a vascular access device (VAD), wherein:

the second optical fiber includes one or more core fibers including a plurality of sensors distributed along a longitudinal length of a corresponding core fiber and each sensor of the plurality of sensors being configured to (i) reflect a light signal of a different spectral width based on received incident light, and (ii) change a characteristic of the reflected light signal based on a shape of the second optical fiber, and the operations further include:

providing an incident light signal to the second optical fiber;

receiving reflected light signals of different spectral widths of the received incident light from one or more of the plurality of sensors; and processing the reflected light signals associated with the one or more of core fibers to determine a three-dimensional (3D) shape of the second optical fiber.

18. The system of claim 17, wherein:

the second optical fiber is (i) physically coupled with the VAD at a first end of the second optical fiber and (ii) physically coupled with the patient simulation block at a second end of the second optical fiber, and obtaining the position and the orientation of the VAD with respect to the patient simulation block includes determining the position and the orientation based on the shape of the second optical fiber.

19. The system of claim 1, wherein the operations further include simulating an identification of one or more blood vessels within the simulated ultrasound image from among the one or more anatomical elements depicted within the simulated ultrasound image.

* * * * *